United States Patent [19]
Iketaki

[11] Patent Number: 5,650,616
[45] Date of Patent: Jul. 22, 1997

[54] APPARATUS AND METHOD FOR ANALYZING SURFACE

[75] Inventor: Yoshinori Iketaki, Oume, Japan

[73] Assignee: Olympus Optical Co., Ltd., Tokyo, Japan

[21] Appl. No.: 390,352

[22] Filed: Feb. 16, 1995

Related U.S. Application Data

[63] Continuation-in-part of Ser. No. 45,218, Apr. 13, 1993, abandoned.

[30] Foreign Application Priority Data

| Apr. 14, 1992 | [JP] | Japan | 4-094508 |
| Feb. 22, 1993 | [JP] | Japan | 5-032092 |
| Feb. 22, 1993 | [JP] | Japan | 5-032093 |

[51] Int. Cl.$^6$ .................. B01D 59/44; H01J 49/00
[52] U.S. Cl. .................. 250/288; 250/305; 250/282; 378/53
[58] Field of Search .................. 250/305, 306, 250/309, 310, 281–283, 288, 287, 286, 289, 358.1, 399, 492.1, 492.3; 378/53

[56] References Cited

U.S. PATENT DOCUMENTS

| H1200 | 6/1993 | Neifeld | 378/119 |
| 3,798,568 | 3/1974 | Willett | 372/82 |
| 3,953,732 | 4/1976 | Oron et al. | 250/282 |
| 4,140,905 | 2/1979 | Polanyi | 250/282 |
| 4,317,994 | 3/1982 | Mallozzi et al. | 378/119 |
| 4,393,311 | 7/1983 | Feldman et al. | 250/459.1 |
| 4,733,073 | 3/1988 | Becker et al. | 250/282 |
| 4,780,608 | 10/1988 | Cross et al. | 250/288 |
| 4,847,493 | 7/1989 | Sodal et al. | 250/282 |
| 5,045,694 | 9/1991 | Beavis et al. | 250/288 |
| 5,138,158 | 8/1992 | Ninomiya et al. | 250/305 |
| 5,164,592 | 11/1992 | Kitamori et al. | 250/288 |

OTHER PUBLICATIONS

Shogo Nakamura, *Physics of Surface*, Kyoritsu Shuppan Kabushiki Kaisha, Dec. 1982, pp. 104–107.

*Primary Examiner*—Bruce Anderson
*Attorney, Agent, or Firm*—Cushman, Darby & Cushman IP Group of Pillsbury Madison & Sutro LLP

[57] ABSTRACT

A surface analyzing apparatus includes a laser plasma radiation source, an optical condensing system for converging ultraviolet light, vacuum ultraviolet light, or X rays emitted from the laser plasma radiation source on the surface of a sample, and a mass spectrometer or a time-of-flight spectrometer for detecting the secondary ions emitted from the sample. Thus, the surface analyzing apparatus is capable of analyzing two-dimensionally adsorbed substances on the sample surface with a high resolving power.

19 Claims, 18 Drawing Sheets

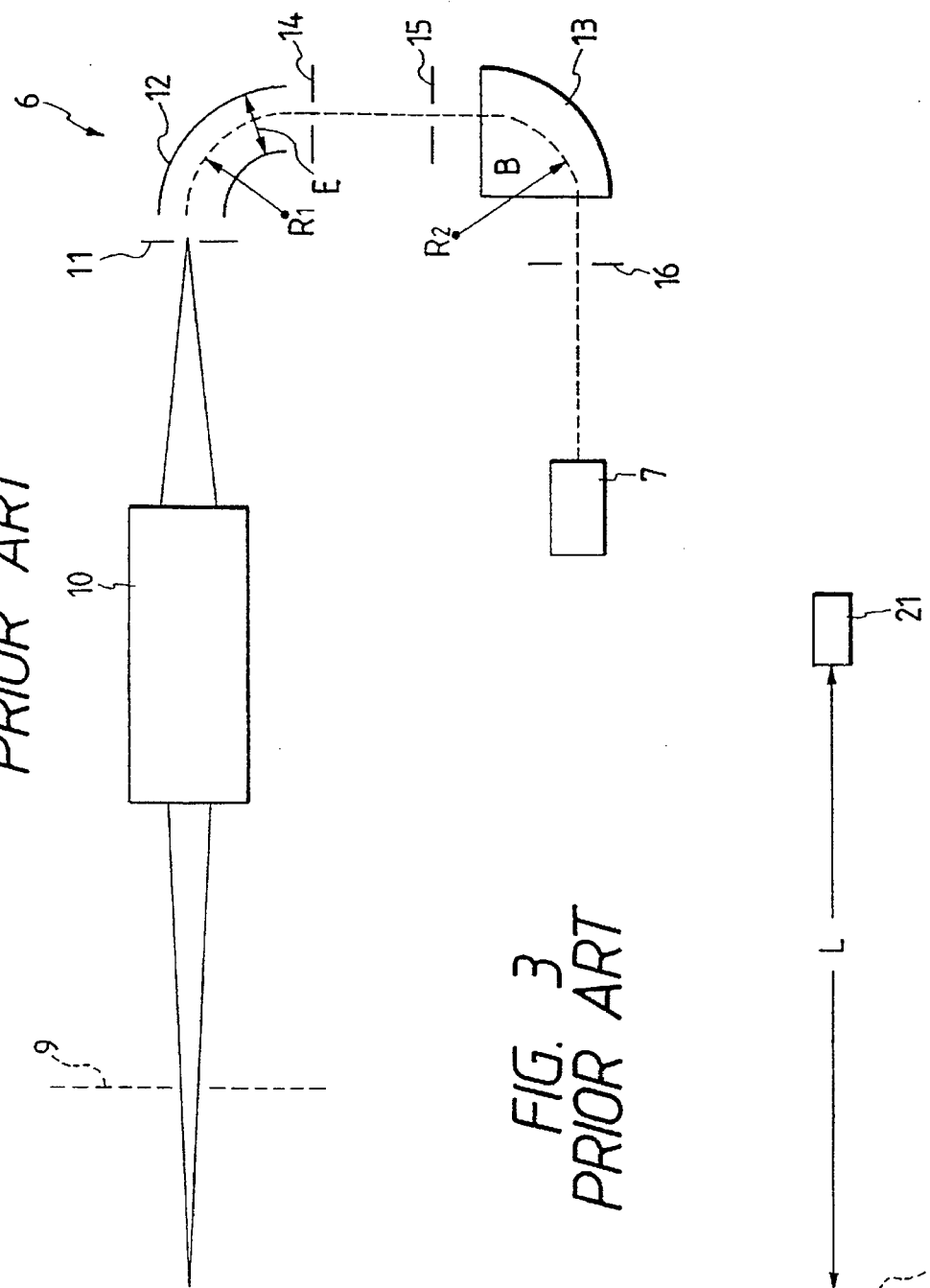

APPARATUS AND METHOD FOR ANALYZING SURFACE

This is a continuation-in-part (CIP) of application Ser. No. 8/045,218, filed on Apr. 13, 1993, now abandoned.

BACKGROUND OF THE INVENTION

1. Field of the Invention

This invention relates to apparatus for and methods of analyzing a surface which use a microbeam of particles of electrons, positrons, ions, neutrons, or photons, such as ultraviolet light, vacuum ultraviolet light, X rays, etc., to analyze elements on the surface of a sample in a destructive or nondestructive way.

2. Description of the Related Art

With the recent development of semiconductor fabricating technology, various methods for surface analysis have been noticed as means of evaluating semiconductor materials. In particular, the analyzing technique of examining the state of contamination on the surface of a silicon wafer is indispensable for a semiconductor fabricating process. The most powerful means of evaluation is the method of removing adsorbed atoms and molecules from the surface of a sample, such as the silicon wafer, analyzing the mass of ions produced, and examining the state of contamination of carbon compounds and water molecules of the sample. Specifically, the methods, such as secondary ion mass spectrometry (SIMS), electron stimulated desorption (ESD), and photon stimulated desorption (PSD), are well known as means of spectrometric analysis. For example, when the surface of the sample is irradiated with fast ions, ionized atoms which constitute the surface of the sample are emitted from the surface as secondary ions. The method of analyzing the mass of the secondary ions is the SIMS.

A conceptual view of the SIMS is given in FIG. 1. Among the elements shown in FIG. 1 are: a CRT 100, a scanning power means 101, an optical microscope 102, amplifiers 103, 108, a secondary electron multiplier 104, a screen electrode 105, a sample holder 106, a recorder 107, a secondary ion extracting electrode 109, a collector slit 110, a sector magnetic field 111, a β slit 112, a sector electric field 113, an objective stop 114, a compensating lens 115, and a slit 116. A beam of ions, such as Cs, emitted from an ion gun 1 pass through a condenser lens 2 and an objective lens 3, and is converged into a spot diameter of 1 μm or less on the surface of a sample 4. The ion beam is deflected when traversing a deflection electrode 5 disposed between the condenser lens 2 and the objective lens 3, and thus can be made scan the sample 4 two-dimensionally by controlling the deflection electrode 5. The secondary ions discharged from the sample surface by irradiation with the ion beam pass through a mass spectrometer 6 and are detected at a secondary electron multiplier 7 by a mass spectrometer. If the ion beam is mass-analyzed by means of the two-dimensional scan, a two-dimensional spatial mapping of a specific element will be possible.

The SIMS shown in FIG. 1 is constructed so that a secondary electron and visible light, in addition to the secondary ion, emitted from the sample surface can also be observed, thus providing a multiple analysis. For the spectrometry of the secondary ion, a time-of-flight spectrometry is sometimes used. This method is analogous to an X-ray microanalyzer by using an electron beam as a probe in view of the fact that the microscopic region of the sample surface can be analyzed. However, it is superior to the X-ray microanalyzer because of the facts that the analysis of isotopic elements is possible and that an analysis sensitivity, notably a detection sensitivity to light elements, is higher. A means of scanning and analyzing the sample surface with an electron beam in the arrangement similar to the SIMS as mentioned above is called the ESD. On the other hand, a means of irradiating and analyzing the sample with light of shorter wavelength than ultraviolet light, using a synchrotron radiation (SR) source or a mercury-vapor lamp, is termed the PSD.

Next, reference is made to the mass spectrometry and the time-of-flight spectrometry which are typical secondary ion spectrometries.

For the mass spectrometry, FIG. 2 is a conceptual view showing the mass spectrometer 6. The secondary ions generated from the surface of the sample 4 (refer to FIG. 1) are accelerated by a secondary ion extracting electrode 9 and converged by a compensating lens 10. They travel through an entrance slit 11 and are selected by a coaxial cylindrical sector electrode 12 and a sector magnet 13. Specifically, since the ions passing through the entrance slit 11, incident on the sector electrode 12 have particular velocity, mass, and electric charges, they are deflected so as to follow the orbit of the sector electrode 12 only where a particular voltage is applied to the electrode 12, and can thus pass through the electrode 12. Subsequently, the ions having traversed the sector electrode 12 are selected, through two slits 14 and 15, by the sector magnetic field produced by the sector magnet 13. The sector magnetic field 13 has such behavior that a magnetic force is applied perpendicular to the orbital plane of the secondary ion and the orbit of the secondary ion is changed by the Lorentz force. According to the arrangement depicted in FIG. 2, two slits 15 and 16 are disposed at the entrance and the exit, respectively, of the region in which the sector magnetic field 13 is present. Whereby, when the secondary ions travel through the sector magnetic field 13, an arcuate orbit can be defined. Hence, by choosing a magnetic flux density, the secondary ion having the particular velocity, mass, and electric charge can pass through the slit 16. The ion thus selected is detected by the secondary electron multiplier 7.

For the secondary ion thus available, a description is made of the method of calculating quantitatively the result of the mass analysis. In the sector electrode 12, the intensity of the sector electric field is designated by E and the orbital radius of the sector electrode by $R_1$, while in the sector magnetic field 13, the magnetic flux density of the sector magnetic field is denoted by B and the orbital radius of the sector magnetic field by $R_2$. The mass of the incident ion is represented by m, the ionic valence number by n, the electronic charge by e, and the velocity of incidence by u. In this case, the condition of the sector electric field that the secondary ion can follow the arcuate orbit of the radius $R_1$ is that an electrostatic force balances with a centrifugal force in the sector electric field. This is given by $$e\, n\, E = m\, u^2 / R_1 \qquad (1)$$

Similarly, the condition of the sector magnetic field 13 that the secondary ion can follow the arcuate orbit of the radius $R_2$ is that the Lorentz force balances with the centrifugal force in the sector magnetic field 13. This is given by $$e\, n\, u\, B = m\, u^2 / R_2 \qquad (2)$$

Elimination of u from Eqs. (1) and (2) yields $$e\, n/m = (R_1/R_2^2)(E/B^2) \qquad (3)$$

Hence, the mass analysis of an arbitrary ion can be made in accordance with the intensities of the sector electric field and the sector magnetic field.

Next, time-of-flight spectrometry is explained. The time-of-flight spectrometer is simpler in system structure than the mass spectrometer, and its conceptual view is given in FIG. 3. In this figure, a sample 18 is placed in the uniform electric field of an electrode 19 to accelerate the secondary ions generated by the irradiation of a laser beam toward a drawing electrode 20. The ion accelerated to the velocity u by passing through the drawing electrode 20 travels a distance L from the position of the electrode 20 and is then detected by a secondary electron multiplier 21.

Now, reference is made to the method of calculating quantitatively the result of the mass analysis based on the time-of-flight spectrometry. If it is assumed that the secondary ions are accelerated at a voltage V, the relation with the velocity u can be written, by the law of conservation of energy, as $$e \; n \; V = (\tfrac{1}{2}) \; m \; u^2 \tag{4}$$

When the distance between the two electrodes 19 and 20 is taken as k, a time $T_0$ required for the secondary ion to travel from the electrode 19 to the drawing electrode 20 is given by $$T_0 = \sqrt{[m/(2 \, e \, n \, V)] k} \tag{5}$$

Because the distance from the electrode 20 to the secondary electron multiplier 21 is L, a time of flight $T_1$ required for the secondary ion to reach the secondary electron multiplier 21 from the electrode 20 becomes $$T_1 = L/u \tag{6}$$

Eq. (6) can be rewritten, in terms of Eq. (4), as $$T_1 = L/\sqrt{(2 \, e \, n \, V/m)} \tag{7}$$

A time T required for the secondary ion produced by the sample 18 to arrive at the secondary electron multiplier 21 which is a detector is $T_0 + T_1$. If, therefore, the time T is measured to determine the voltage V, en/m can be found. In general, where the time at which the ion has been produced is specified, the time-of-flight spectrometry may be more convenient because of its simpler structure.

The SIMS, PSD, and ESD, although they are powerful means for the surface analysis as mentioned above, have individually some problems. Specifically, each of the SIMS and ESD, in which the probe is corpuscular radiation, has the problem that it is basically a destructive analysis means. Furthermore, the SIMS also has the problem that its ion source is unstable and the energy of incidence of the ion beam largely fluctuated. Also, for controlling the shape of a particle beam, such as ions and electrons, it is required to provide a complicated magnetic or electric field type lens and many high-voltage powers of several tens of kilovolts or more. The resultant system is very complicated and high in cost. The PSD, on the other hand, is a nondestructive analysis means and makes the analysis without introducing an effective imaging element in the X-ray region of several hundred angstroms or less. Consequently, the two-dimensional mapping by the microbeam was impossible. Moreover, this spectrometry must use, as a radiation source, a large-scale, expensive SR source, or a mercury-vapor lamp which is low in intensity and emits only the radiation of long wavelengths of several tens of nanometers or more. Thus, the system utilizing such a source had little practical use.

SUMMARY OF THE INVENTION

It is, therefore, a primary object of the present invention to provide a surface analyzing apparatus which is capable of analyzing two-dimensionally the distribution of elements on the surface of a sample in a nondestructive way and by means of a microbeam.

Another object of the present invention is to provide a surface analyzing apparatus which is capable of analyzing two-dimensionally the distribution of elements on the surface of a sample by an optical microbeam, which is stable, without using a particle beam, X rays, etc.

Still another object of the present invention is to provide a secondary electron spectrometry which is capable of determining accurately the absolute value of energy of the secondary electrons emitted from the sample.

A further object of the present invention is to provide a secondary electron spectrometry which is capable of analyzing, with a high degree of accuracy, the secondary electrons emitted from the sample, using a pulse radiation source.

According to one aspect of the present invention, the surface analyzing apparatus includes a laser plasma radiation source, an optical condensing system for converging ultraviolet light, vacuum ultraviolet light, or X rays emitted from the laser plasma radiation source on the surface of the sample, a mass spectrometer or time-of-flight spectrometer for detecting the secondary ions emitted from the sample. Thus, by the two-dimensional scan of the sample, it is possible to make the surface analysis with a high-level spatial resolving power.

According to another aspect of the present invention, the surface analysis apparatus is equipped with a radiation source emitting a laser beam, an optical deflecting system having a plurality of reflecting surfaces for reflecting the laser beam and rotating around a rotary axis, and a mass spectrometer or time-of-flight spectrometer for detecting the secondary ions emitted from the sample. By the rotation of the reflecting surfaces and the deflection of the rotary axis of the optical deflecting system, the laser beam is converged on the surface of the sample in a vacuum chamber.

According to still another aspect of the present invention, the sample placed in a sample chamber is irradiated with corpuscular radiation so that the secondary electrons are discharged, and they are detected through an electron spectrometer by a detector for measurement of their spectra. In this case, a gas having a known secondary electron resonance line is introduced in the sample chamber, which is then sealed up, and the measured value of energy of the secondary electron is calibrated based on the measured value of energy of the secondary-electron resonance line of the gas.

According to a further aspect of the present invention, the sample is irradiated with corpuscular radiation in a pulse mode so that the secondary electrons are emitted, and they are made incident through an electron spectrometer on a detector and analyzed based on the peak value of an output signal of the detector.

These and other objects as well as the features and advantages of the present invention will become apparent from the following detailed description of the preferred embodiments when taken in conjunction with the accompanying drawings.

BRIEF DESCRIPTION OF THE DRAWINGS

FIG. 2 is a schematic view showing a mass spectrometer of the prior art;

FIG. 3 is a schematic view showing a time-of-flight spectrometer of the prior art;

DETAILED DESCRIPTION OF THE PREFERRED EMBODIMENTS

Before undertaking the description of the embodiments of the present invention, reference is made to the apparatus for analyzing two-dimensionally a surface in a nondestructive way, using a laser plasma radiation source. Recently, with the advent of the SR source, the technology of utilizing radiation in a soft X-ray region has become familiar. This leads to the development of imaging optical systems, detectors, and filters in the soft X-ray region. For the radiation source, the laser plasma radiation source, in addition to the SR source, has lately been put into practical use.

Here, a description is made of the laser plasma radiation source and the soft X-ray imaging optical system which play an important role in the present invention. The laser plasma radiation source is first explained. When a high intensity laser beam is concentrated on a target in a vacuum, plasma of high temperature and density is generated and white X rays of wavelengths more than several angstroms are produced at a high conversion efficiency of about 10%. Such is the laser plasma radiation source, which, compared with the SR source and the X-ray tube, has some attractive features in that it is:

(1) basically a white radiation source with high luminance, (2) a divergent radiation source, unlike the SR source, (3) an ideal pulse radiation source because the pulse width of radiation is identical with that (10 nm sec or less) of the laser, and (4) an ideal X-ray radiation source for laboratory use (namely, suitable for use at the level of laboratories) which is low in cost and compact in size.

Figure 1:
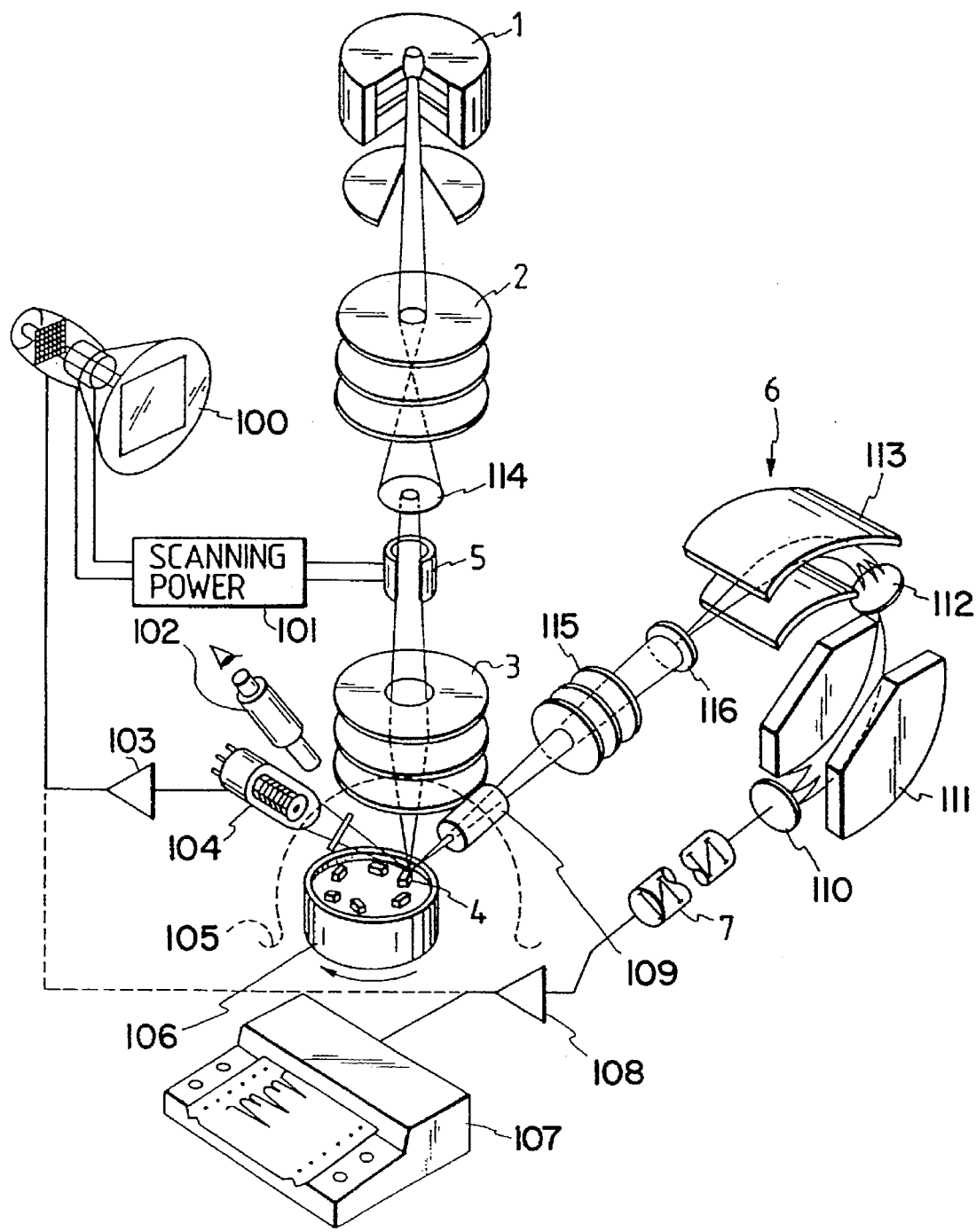
FIG. 1 is a schematic view showing the SIMS of a surface analyzing apparatus of the prior art.
Figure 4:
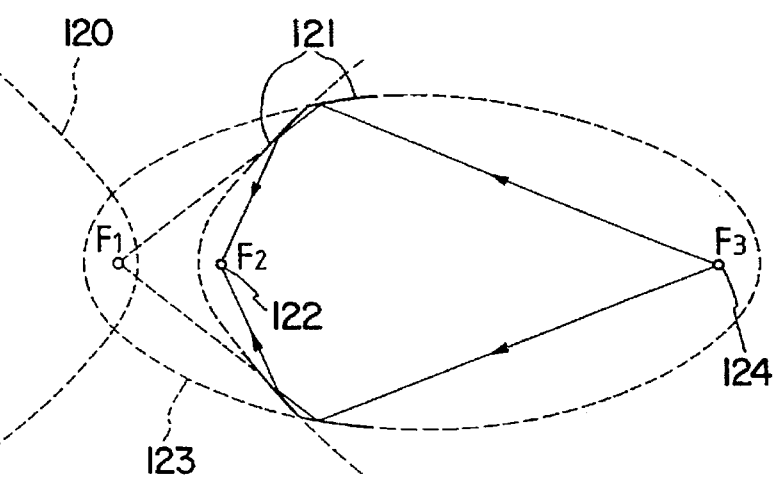
FIG. 4 is a view showing the principle of a Wolter optical system.
Figure 5A:
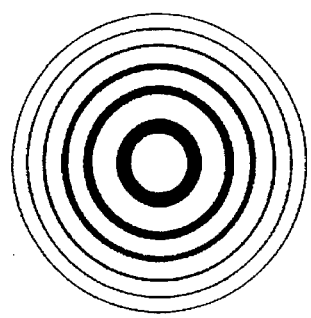
FIGS. 5(a) and 5(b) are views showing the principle of a zone plate.
Figure 5B:
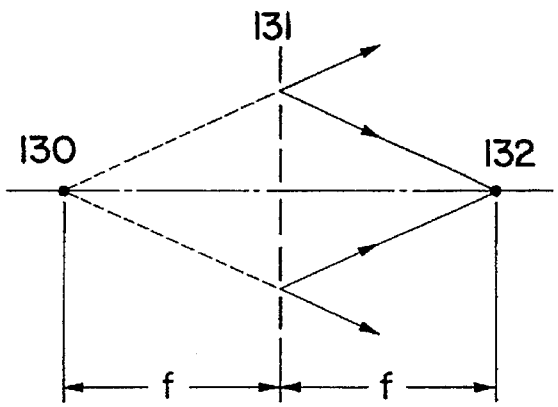
Figure 6:
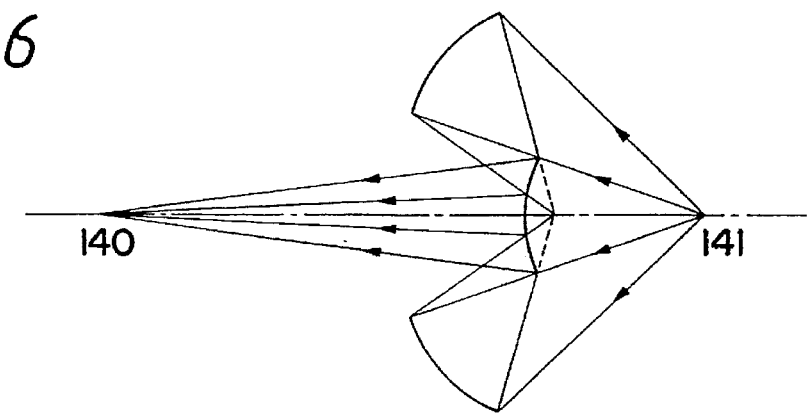
FIG. 6 is a view showing the principle of a Schwarzschild optical system.

Next, the soft X-ray imaging optical system is explained. The soft X-ray imaging optical system which is a powerful tool in the field of an X-ray microscope at present is available in three types: an optical system using a grazing incidence reflecting mirror, such as the Wolter type, shown in FIG. 4, a zone plate utilizing diffraction in FIG. 5, and a normal incidence optical system, such as a Hoffner or Schwarzschild optical system having a reflecting mirror whose surface is coated with a multilayer film, shown in FIG. 6. Also shown in FIG. 4 are: the hyperboloid of revolution 120, reflecting surfaces 121, the image point 122, the ellipsoid of revolution 123, and the object point 124. Also shown in FIG. 5(b) are: the focal point (virtual image) 130, the zone plate 131, and the focal point (real image) 132. Also shown in FIG. 6 are the image point 140 and the object point 141. These three types of optical systems have features different from one another. The optical system using the grazing incidence reflecting mirror permits imaging of white radiation containing X rays with a high resolving power of about 50 nm. The zone plate possesses spectral performance, along with imaging performance, and converges radiation at different places in accordance with wavelengths used. Thus, by choosing a point for convergence, the radiation of an arbitrary monochromatic wavelength can be imaged. The normal incidence optical system, on the other hand, can image only the X rays of particular wavelengths because of a spherical mirror coated with the multilayer film having a wavelength dispersion property, but has a larger NA, with a resultant wider visual field, and can form the image of an object with a high resolving power of several tens of nanometers.

Making use of the laser plasma radiation source and the soft X-ray imaging optical system mentioned above, the present invention has made it possible to realize the surface analyzing apparatus which is a secondary ion spectrometer for surface analysis.

Figure 7:
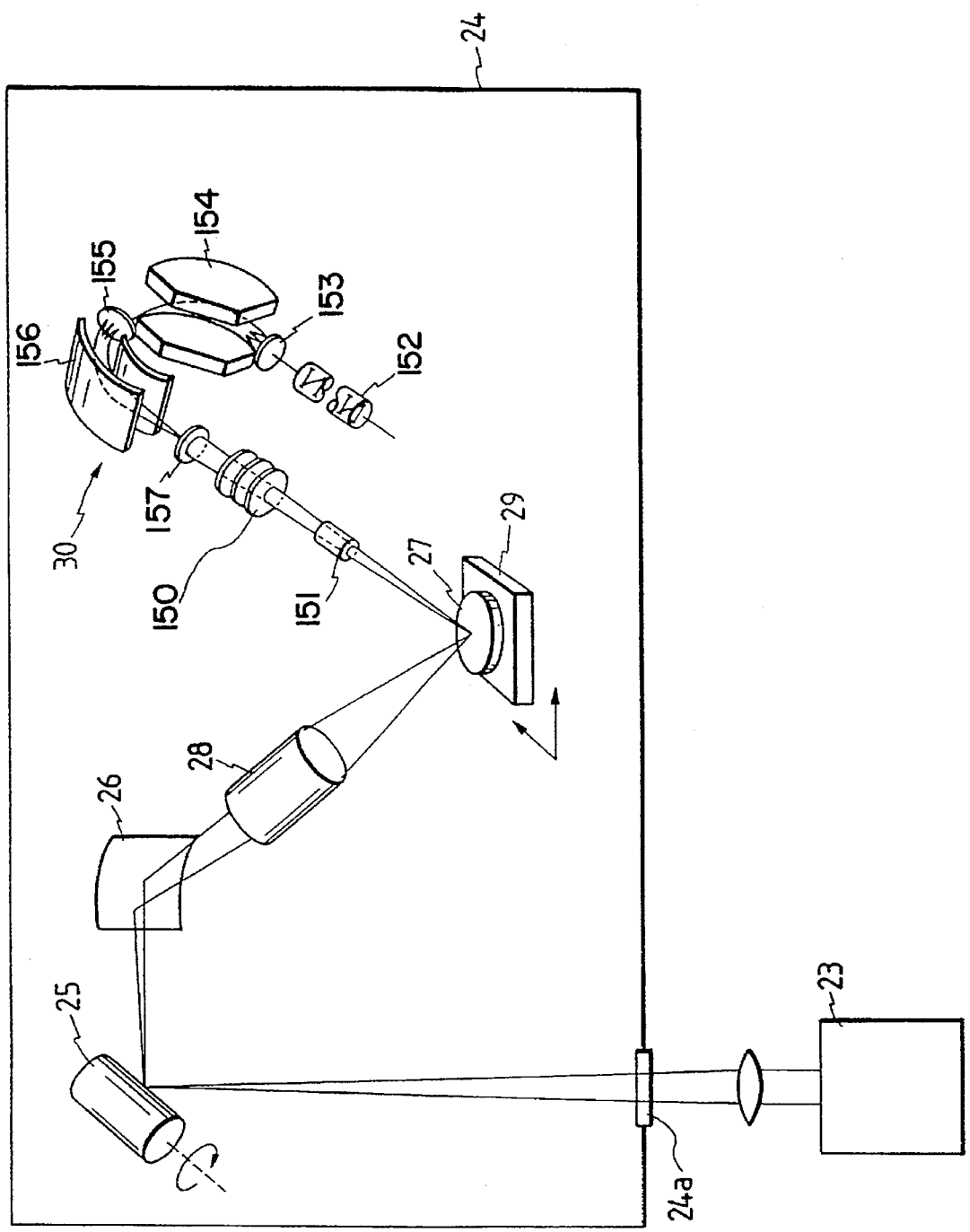
FIG. 7 is a view showing a fundamental arrangement of a surface analyzing apparatus according to the present invention.

The fundamental arrangement of the present invention is given in FIG. 7. In the surface analyzing apparatus according to the present invention, a vacuum chamber 24 having an optical window 24a on which a laser beam from a YAG laser 23 is incident contains a rotary target 25 which, when irradiated with the laser beam, resolves its part into plasma to produce ultraviolet light, vacuum ultraviolet light, or X rays. The apparatus further includes a monochrometer 26, such as a grating, receiving radiation emitted from this laser plasma radiation source to produce monochromatic radiation, and an optical condensing system 28 converging the monochromatic radiation on the surface of a sample 27.

The optical condensing system 28 is composed of a soft X-ray imaging optical system converging X rays from the target 25 into a spot diameter, for example, of 0.1 μm or less, on the sample 27. A sample stage 29 on which the sample 27 is placed is situated so that it is scanned two-dimensionally. Further, a mass spectrometer 30, or a time-of-flight spectrometer, detecting secondary ions emitted from the sample 27 is provided on the orbit of the ions. In the arrangement shown in FIG. 7, the mass spectrometer 30 is thus used as an ion detector, and because the laser plasma radiation source is an ideal pulse radiation source, the production time of the secondary ions can be specified. In this way, even the time-of-flight spectrometer of a simpler structure is capable of analyzing the ions with a high sensitivity by time-of-flight spectrometry. Also shown in FIG. 7 are: a compensating lens 150, a secondary ion extracting electrode 151, a secondary electron multiplier 152, a collector slit 153, the sector magnetic field 154, a β slit 155, the sector electric field 156, and a slit 157.

Next, reference is made to the surface analyzing apparatus according to the present invention which makes the surface analysis by means of an optical microbeam, which is stable. When the laser beam is converged on the sample in a vacuum, parts of substances adsorbed on the surface of the sample and the sample surface are resolved to cause ablation. If these scattered substances are analyzed in terms of the secondary ions, it is possible to make the surface analysis equivalent to the SIMS, PSD, and ESD. The surface analyzing apparatus according to the present invention, which applies this principle, is provided with a laser radiation source, an optical deflecting system deflecting laser beam emitted from the laser radiation source to irradiate the sample disposed in a vacuum with the deflected laser beam, and a mass spectrometer or a time-of-flight spectrometer mass-analyzing the secondary ions emanating from the sample surface.

In the present invention using the laser plasma radiation source, the radiation emitted from the laser plasma radiation source is converted into monochromatic radiation by the monochrometer 26 and converged on the sample 27 by the optical condensing system 28. By moving two-dimensionally the sample stage 29, the radiation is made scan on the sample 29 two-dimensionally. In this case, X rays as a probe do not entirely cause damage to the surface of the sample 27. Further, the selection of the wavelength of X rays by the monochrometer 26 or the optical condensing system 28 makes it possible to dissociate a molecule of in which an analyzer has an interest. Hence, the analysis can be made with a high sensitivity. The secondary ions emanating from the surface of the sample 27 traverse the mass spectrometer or time-of-flight spectrometer 30 and are detected by a secondary electron multiplier, such as a photomultiplier or a microchannel plate (MCP), for two-dimensional mapping.

As for the surface analyzing apparatus according to the present invention using the laser radiation source, the laser beam from the laser radiation source is deflected by means of the optical deflecting system, such as a polygonal rotating mirror, disposed in the atmosphere, not in a vacuum. Thus, the laser beam, as the probe, can easily scan the sample surface. Moreover, by adjusting the power of the laser beam, it is possible to minimize the damage of the sample surface and dissociate only the adsorbed substances of the sample surface. Conversely, by resolving gradually the sample surface, the analysis of components is also possible in a direction of depth identical with the SIMS and ESD. The laser radiation source, which is an ideal pulse radiation source, has the advantage that the production time of the secondary ions can be specified and even where the time-of-flight spectrometer of a simpler structure, instead of the mass spectrometer, is used, the ion analysis can be made with a high sensitivity by the time-of-flight spectrometry.

Referring to the drawings shown, the preferred embodiments of the present invention will be explained in detail below.

Figure 8:
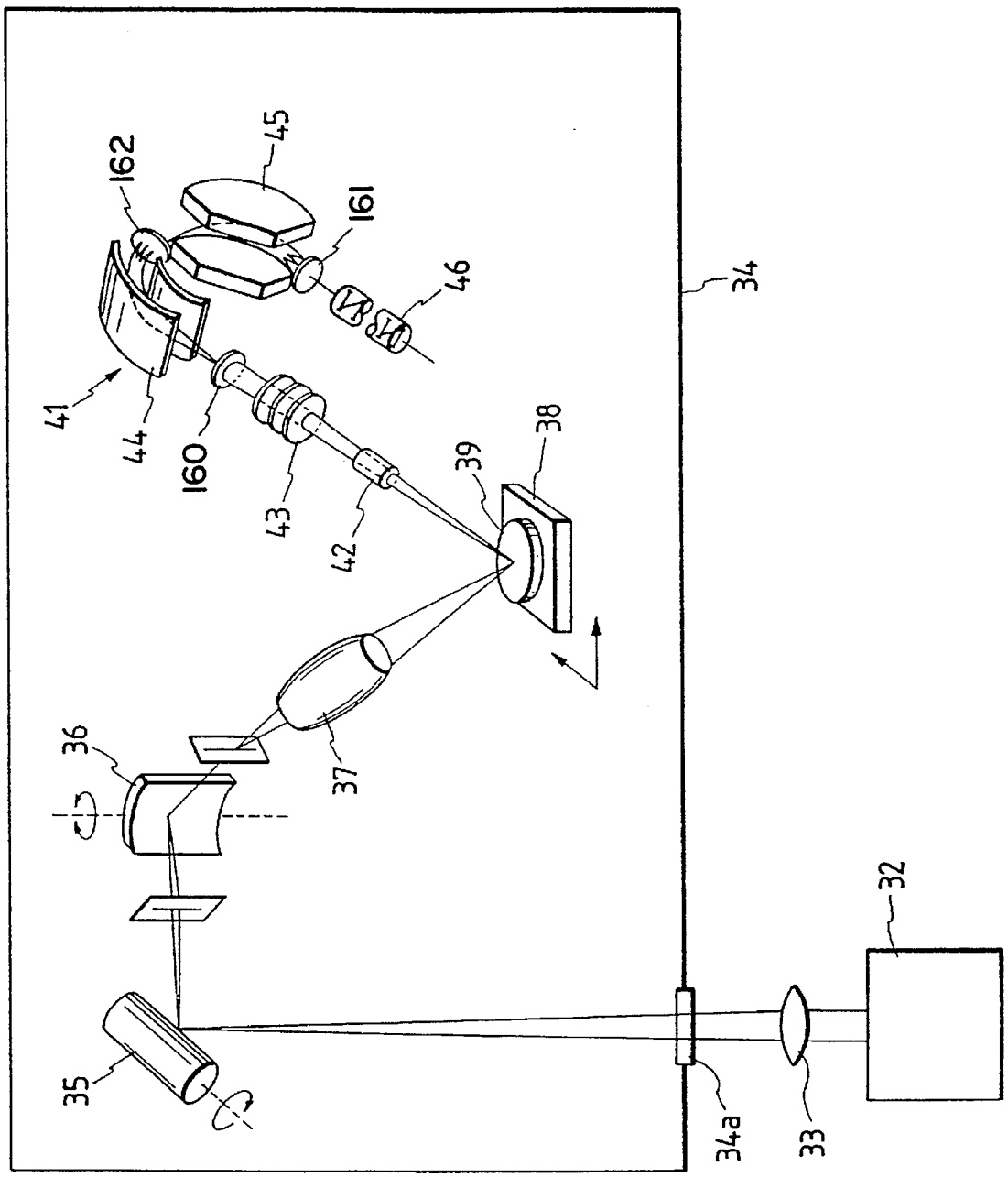
FIG. 8 is a view showing the arrangement of a first embodiment of the surface analyzing apparatus according to the present invention.

FIG. 8 is a schematic view of the arrangement of the surface analyzing apparatus showing a first embodiment of the present invention. In this figure, a YAG laser 32 emitting an Nd:YAG laser beam and a collector lens 33 situated in front thereof are disposed in the atmosphere. A vacuum chamber 34 on which the Nd:YAG laser beam is incident through an optical window 34a contains a rotary target 35 which, when irradiated with the laser beam, resolves its part into plasma to produce, for example, white soft X rays from the plasma of high temperature and density. The target 35 is constructed so that when its part evaporates and caves in because of the irradiation, the laser beam strikes a new surface of the target rotated. These constitute the laser plasma radiation source. Also shown in FIG. 8 are a slit 160, a collector slit 161, and a β slit 162.

The produced soft X rays are monochronized by a monochrometer 36, for which, as an example, a Seya-Namioka type monochrometer having a constant-deviation angle is used. With the monochrometer 36, the wavelengths of the X rays can be selected and the sample is irradiated with the radiation of photon energy corresponding to bond energy of particular molecules. In this way, an interesting secondary ion can be selectively detected.

A Wolter type condenser lens 37 disposed in front of the optical path of the monochrometer 36 is adapted to converge the soft X rays emanating from the monochrometer 36 into a spot diameter of approximately 0.1 μm on the surface of the sample 39 placed on an XY stage 38, thereby producing the secondary ions from the sample surface. The XY stage is moved in an XY direction to cause the soft X rays to scan the sample 39 two dimensionally.

A mass spectrometer 41, such as is described above, is disposed on the orbit of the secondary ions produced from the sample 39. The mass spectrometer 41 includes a secondary ion extracting electrode 42, followed by a compensating lens 43, and a sector electrode 44 and a sector magnetic field 45 which select the secondary ion having the particular velocity, mass, and electric charge. The mass spectrometer 41 is then connected to a secondary electron multiplier 46 which detects the selected secondary ion.

The first embodiment is constructed as mentioned above. Thus, the laser beam emitted from the YAG laser 32 enters the vacuum chamber 34 and irradiates the rotary target 35. A part of the target 35 is thereby dissolved into plasma, from which soft X rays are generated. White soft X rays produced from the laser plasma radiation source is monochronized by the monochrometer 36 and converged on the sample 39 by the Wolter lens 37. Consequently, the secondary ions are produced from the sample surface. The secondary ions, after being accelerated by the secondary ion extracting electrode 42, pass through the electrostatic compensating lens 43. They are then selected by the sector electrode 44 and the sector magnetic field 45 which act as secondary ions deflecting means, and detected by the secondary electron multiplier 46.

Since in particular the wavelength is selected by the monochrometer 36, the sample 39 can be irradiated with the radiation of photon energy corresponding to bond energy of particular molecules and an interesting secondary ion can be selectively detected. Thus, in the mass analysis, the signals can well be detected with a good S/N ratio. Further, the two-dimensional scan of the sample 39 by the movement of the XY stage 38 in the XY direction makes it possible to analyze the surface with an extremely high spatial resolving power of a sub-μm level. In the case where the analysis is made without limitation to the particular molecules, it is only necessary to converge directly the white radiation through the Wolter lens 37, not through the monochrometer 36, on the sample surface.

Figure 9:
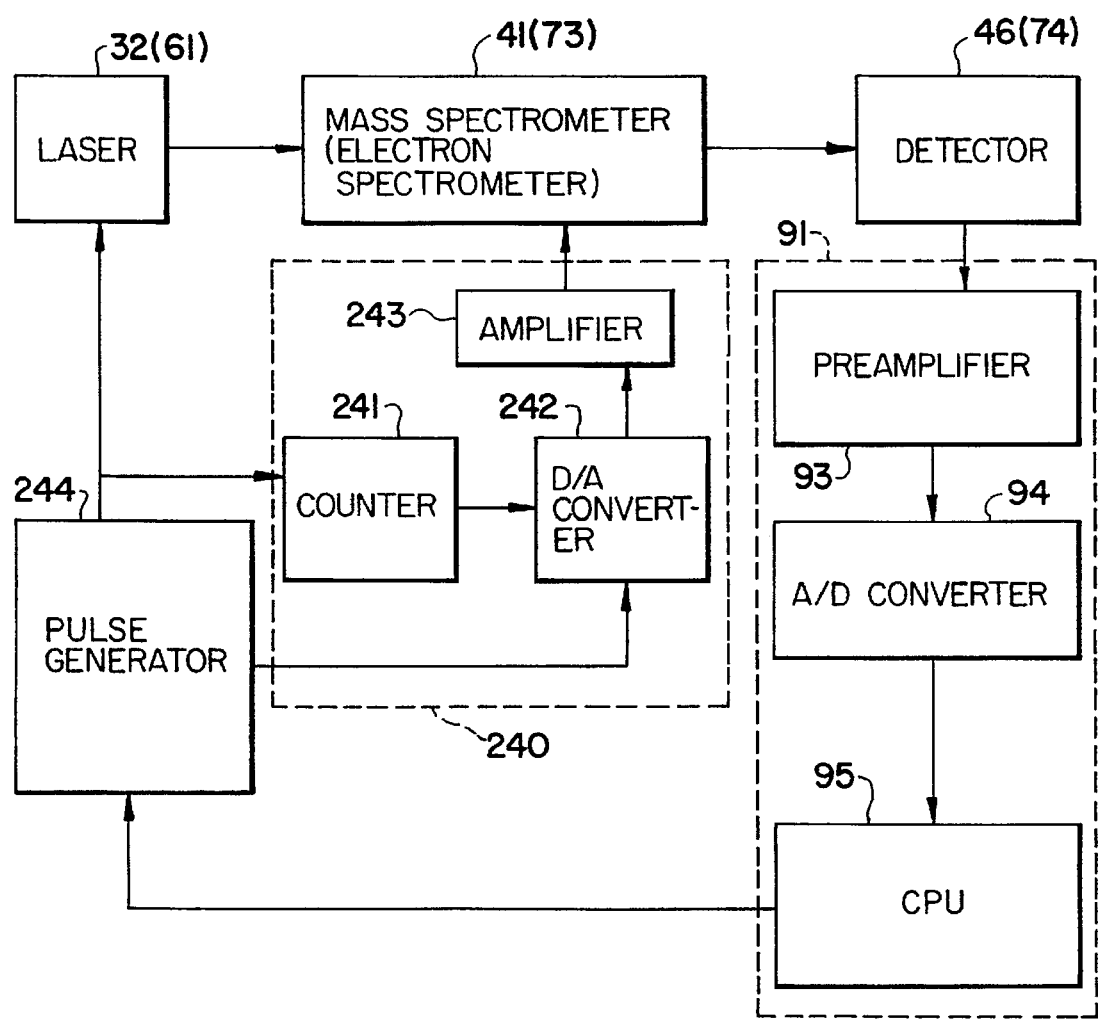
FIG. 9 is a diagram showing a circuit arrangement of the surface analyzing apparatus according to the present invention.
Figure 10:
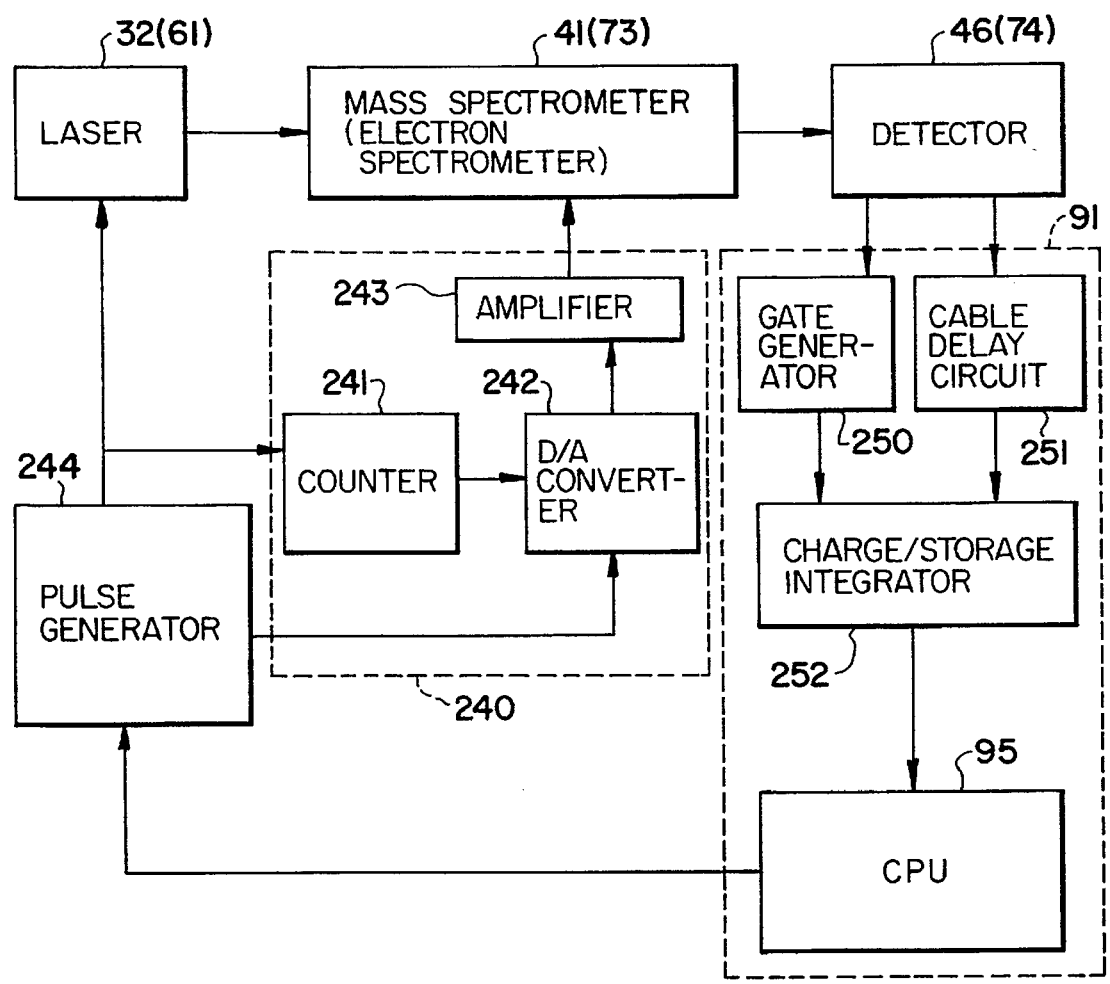
FIG. 10 is a diagram showing another circuit arrangement of the surface analyzing apparatus according to the present invention.
Figure 11A:
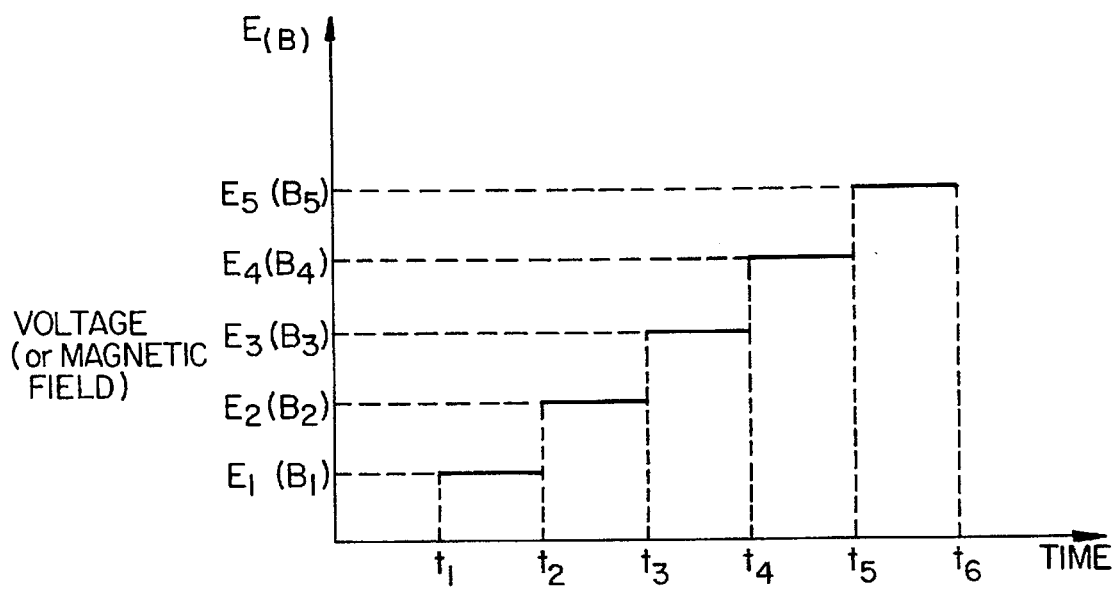
FIG. 11A shows control of voltage or magnetic field applied to the secondary ions deflecting means.
Figure 11B:
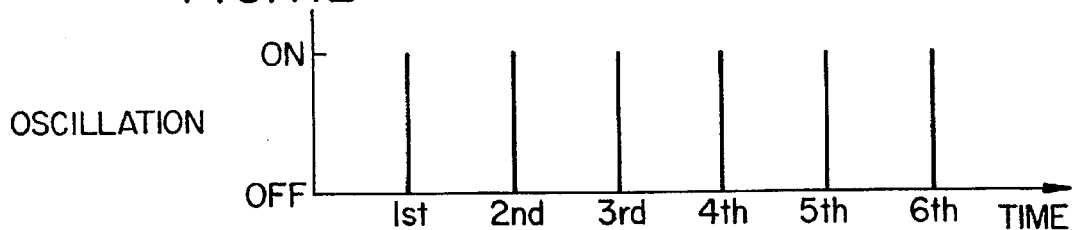
FIG. 11B shows oscillation of laser pulse.

The selection by the sector electrode 44 and the sector magnet 45, which act as the secondary ions deflecting means, is described as follows. FIG. 9, where none of the elements arranged between the laser 32 of the laser plasma radiation source and the mass spectrometer 41 including the sector electrode 44 and the sector magnet 45 is shown, is a circuit diagram illustrating an arrangement for detecting output signals from the secondary electron multiplier 46 in FIG. 8. Since the source of radiation utilized is a laser plasma radiation source comprising a laser 32 which generates laser beam in pulse mode, each time a pulse of the laser beam is generated, a pulse of soft x ray is generated at the target 35 in FIG. 8 for irradiation of the sample and consequently secondary ions are emitted from the sample. Of the secondary ions varying in energy state, those possession particular energy are selected responding to an electric field having particular strength (in terms of voltage applied) or a magnetic field having particular strength, the former being formed abut the section electrode 44 and the latter about the sector magnet 45. To achieve such selection, the laser beam in pulse mode is synchronized with forming of an electric field about the sector electrode 44 in terms of voltage application or forming of a magnetic field about the sector magnet 45. For instance, as seen from FIGS. 11A and 11B, for a time period t1–t2 which starts at a particular time point after generation of a first pulse set of the laser beam, voltage applied to the sector electrode 44 or magnetic flux density of the magnetic field about the magnet 45 is maintained at a particular value (E1 or B1), thereby secondary ions possession certain energy which responds to the constant voltage (E1) or the constant magnetic flux density (B1) being detected. For the purpose of controlling voltage applied to the sector electrode 44 to be the constant value (E1), deflection amount control means 240 comprising a counter 241, a D/A converter 242 and an amplifier 243 is provided as shown in FIG. 9. The counter 241 counts number of pulse sets of the laser beam generated. The D/A converter 242 and the amplifier 243 control amount of deflection at the secondary ions deflecting means in accordance with number of pulse sets counted. After a first pulse set shown in FIG. 11B is generated, voltage (or magnetic flux density) is controlled to be E1 or (B1) for a time period of t1–t2 as shown in FIG. 11A; after a second pulse set, voltage (or magnetic flux density) is maintained at E2 (or B2) for t2–t3; after a third pulse set, maintained at E3 (or B3) for t3–t4. The counter 241 is dispensable if a pulse generator 244 is built in a CPU 95. Secondary ions thus selected are detected at the secondary electron multiplier 46 and then analyzed in a measuring section 91. The measuring section 91 includes a resistance 92 not shown in the drawing, a preamplifier 93, an A/D converter 94 and the CPU 95 so that a charge generated at the secondary electron multiplier 46 is integrated to obtain a voltage peak value and then the voltage peak value is amplified by the preamplifier 93 and converted into a digital signal by the A/D converter 94, to be analyzed by the CUP 95. The analysis of the secondary ions in the measuring section 91 can be performed with an alternative structure in which a gate generator 250, a cable delay circuit 251 and a charge-storage integrator 252 are arranged as shown in FIG. 10. The gate generator 250 generates a signal for determining whether the signal from the secondary electron multiplier 46 is to be sent to the charge-storage integrator 252 or not. The cable delay circuit 251 delays transmission of the signal from the secondary electron multiplier 46 to the charge-storage integrator 252. In accordance with timing determined by the gate generator 250 and the cable delay circuit 251, the signal from the secondary electron multiplier 46 is sent to the charge-storage integrator 252. The charge-storage integrator 252 integrates the charge signal from the secondary electron multiplier 46 so that a value obtained through the integration can be utilized for analysis of the secondary ions by the CPU 95.

Figure 11C:
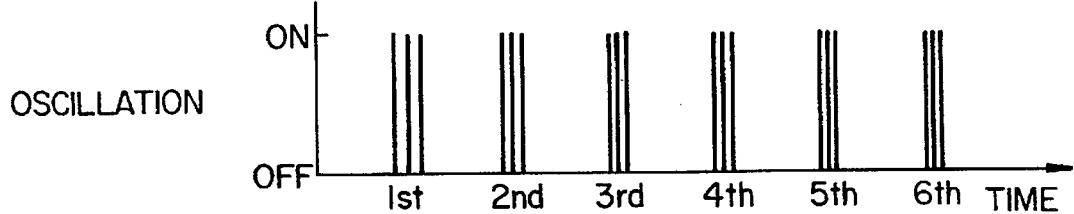
FIG. 11C shows oscillation of laser pulse where a pulse set consists of a plurality of pulses.

If a pulse train of the laser radiation generated from the laser 32 is formed so that each of pulse sets consists of a plurality of pulses as shown in FIG. 11C, a plurality of pulses of soft X rays is generated as one pulse set of soft X rays. Accordingly, secondary ions are emitted multiple times for each irradiation of the sample with a pulse set of the soft X rays. Therefore, signal strength to be detected at one time at the secondary electron multiplier 46 is heightened and thus detection sensitivity is improved, which is preferable. To generate the plurality of pulses included in a pulse set, the circuit may be arranged in such a manner that one pulse generating signal from the pulse generator 244 triggers the laser 32 to generate the plurality of pulses included in a pulse set of the laser radiation, or in such a manner that a plurality of pulse generating signals from the pulse generator 244 triggers the laser 32 to generate respective ones of the plurality of pulses included in a pulse set.

Measurement according to the present invention is different from the conventional pulse-counting method. Not like the laser plasma radiation source generating pulsed soft X rays having high peak value to be reached at an instant, a radiation source used for the measurement according to the pulse counting method is such as a synchrotron or an X-ray tube continuously radiating feeble soft X-rays. Therefore, according to the pulse-counting method, secondary ions emitted from the sample sparsely appear at arbitrary time points in the period of irradiation and those having particular energy are counted one by one as detected. Spectrometry of energy state of secondary ions is achieved by making voltage to be applied to the sector electrode or strength of magnetic field to be formed about the sector magnet of the mass-spectrometer vary linearly as a function of time. If such voltage sweep is utilized, energy state of secondary ions to be detected at the secondary electron multiplier is sweep-scanned according as the voltage varies. Therefore, according to the conventional method, in order to heighten the signal intensity to be obtained, rounds of scanning of energy spectrum of secondary ions over a desired energy range by generating sweep with respect to voltage or magnetic field applied to the mass spectrometer should be performed repeatedly to accumulate values resulted from the counting during respective scanning rounds. In contrast, according to the present invention, since secondary ions emitted at one time as a result of irradiation with the pulsed soft X-rays have substantial energy as a whole, accumulation of resulted values through repeated operation rounds is not always necessary, which fact could shorten time to be taken for measurement. Furthermore, since the apparatus and method according to the present invention do not require linear sweep of the voltage applied, precise control of the sweep is not necessary.

Two-dimensional measurement of the sample is performed as described below. After a certain energy range of secondary ions is scanned as shown in FIG. 11A for a certain spot (first spot) on the sample. XY stage 38 shown in FIG. 8 is displaced in X and Y directions so that another spot (second spot) on the sample is irradiated and the same energy range of secondary ions as scanned for the first spot is scanned. The same procedure is repeated to achieve two-dimensional (spatial) scanning on the sample. If energy of secondary ions to be detected is limited to a narrow range, as exemplified in a case where only energy of ions responding to the applied voltage level E1 in FIG. 11A is to be detected, movement of the XY stage 38 can be arranged to be synchronized with signals from the pulse generator 244. A result of the measurement is obtained as a two-dimensional distribution of secondary ions having energy responding to the applied voltage level E1 on the sample in XY directions. If energy range to be scanned is wide, movement of XY stage 38 is controlled in accordance with number of signals ever generated from the pulse generator 244. The surface analyzing apparatus according to the first embodiment also becomes a spectrometer providing a larger amount of information by monitoring fluorescent X rays, photoelectrons, and Auger electrons, as in the ordinary SIMS.

Figure 15:
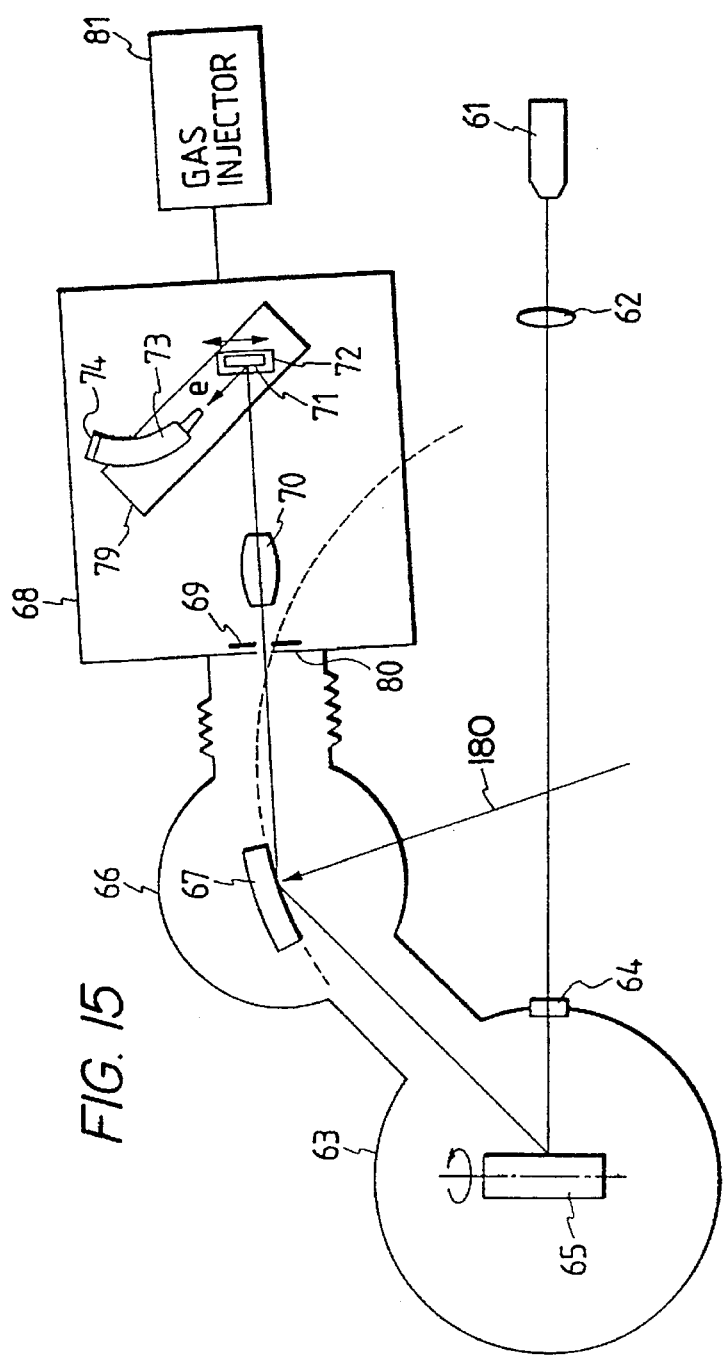
FIG. 15 is a view showing the arrangement of a fifth embodiment of the present invention for measuring the secondary electron.
Figure 16:
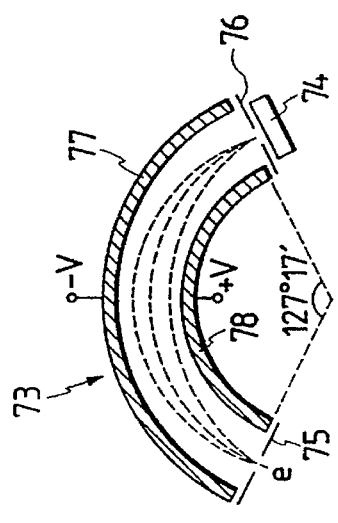
FIG. 16 a view showing an electron spectrometer in the fifth embodiment.

While the description above is made on the first embodiment according to which secondary ions are emitted from the sample, similar technique of measurement is applicable to a case where a sample emits secondary electrons instead of secondary ions, upon arranging an electron spectrometer in place of the mass spectrometer for the purpose of detecting secondary electrons emitted from the sample. For example, if application of the circuit arrangement shown in FIG. 90 to an embodiment supported by FIG. 15 is considered, FIG. 9 and FIG. 15 in combination can support such a modification consistently upon replacing the mass-spectrometer 41 and the secondary electron multiplier 46 appearing in FIG. 9 by an electron spectrometer 73 and a MCP 74 shown in FIG. 15 respectively. Since the electron spectrometer 783 includes cylindrical electrodes 77 and 78 for deflecting secondary electrons as shown in FIG. 16, selection of secondary electrons can be performed by applying variable electric field to the electrodes 77 and 78 as applied to the electrode 44 of the mass spectrometer 41 according to the first embodiment. In general, electric field or magnetic field applied to secondary electron deflecting means included in an electron spectrometer is changeable. For controlling such change, deflection amount control means similar to that indicated by 240 in FIG. 9 would be provided.

Furthermore, although the description above is made on an embodiment where the radiation source is a laser plasma radiation source, a radiation source for irradiating a sample with laser beam in pulse mode can be applied instead. In this case, secondary ions or secondary electrons are emitted from the sample, and detection is performed utilizing appropriate spectrometric means (a mass spectrometer or an electron spectrometer) and the accompanying deflection amount control means as described above.

In the first embodiment, as mentioned above, the adsorbed substances on the sample surface can be analyzed two-dimensionally with the high resolving power in the nondestructive way. Since the laser plasma radiation source is used as the radiation source, the apparatus is low in cost and compact in size. Furthermore, since photoelectrons and Auger electrons can be analyzed at the same time, a multiple analysis is possible.

Figure 12:
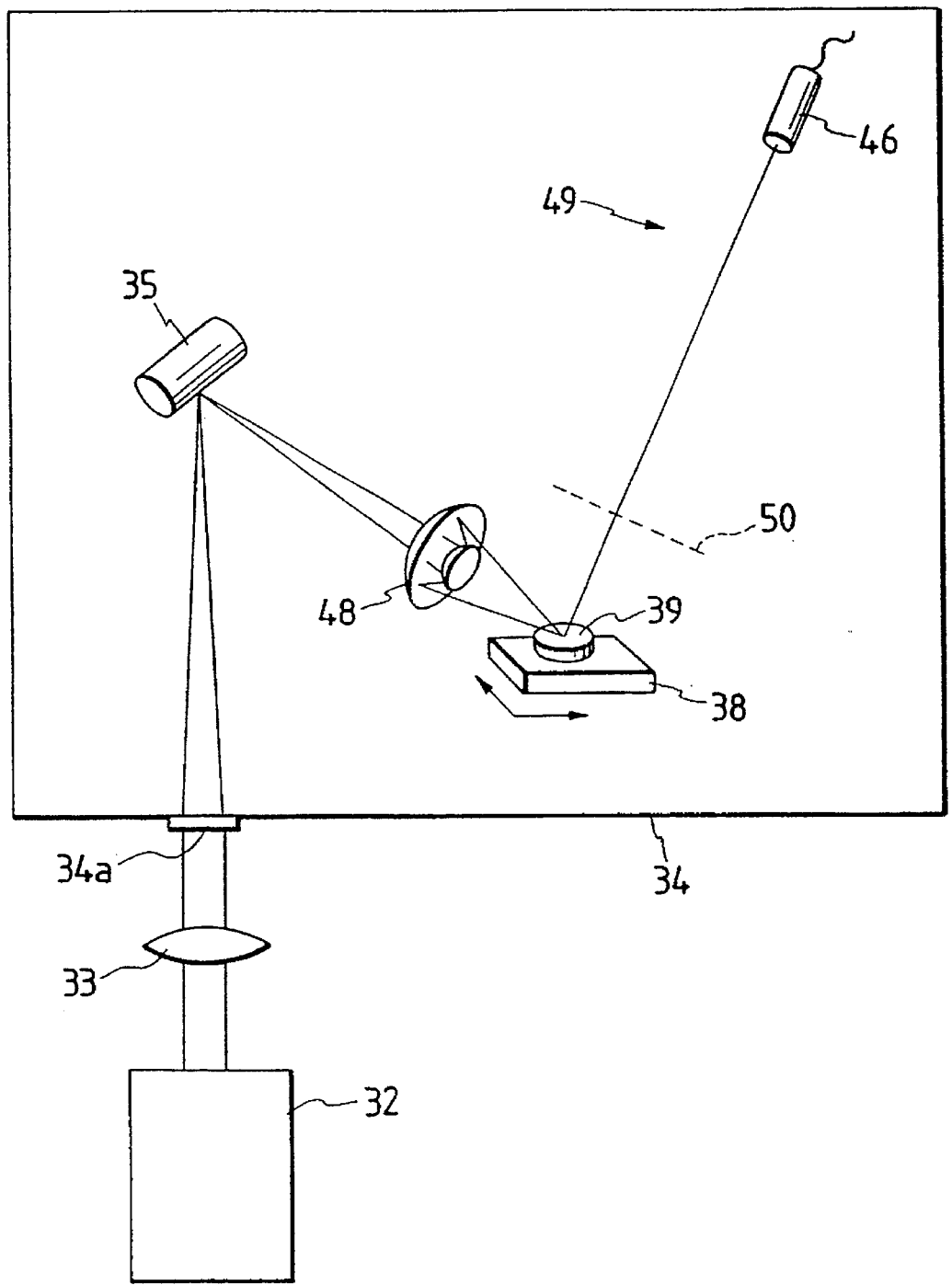
FIG. 12 is a view showing the arrangement of a second embodiment according to the present invention.

Next, based on FIG. 12, a description is given of a second embodiment of the present invention, in which like reference numerals are used to designate like members or parts with the first embodiment. FIG. 12 shows a schematic view of the arrangement of the surface analyzing apparatus in which the mass analysis of the secondary ions is made by time-of-flight spectrometry. In this embodiment, a Schwarzschild optical system 48 is disposed instead of the monochrometer 36 and the Wolter condenser 37. The white soft X rays emitted from the laser plasma radiation source are monochronized by the optical system 48 and converged with a spot diameter of at least 0.1 μm on the sample 39. A time-of-flight spectrometer 49 is disposed on the orbit of the secondary ions produced by the sample 39. The time-of-flight spectrometer 49 includes a secondary ion extracting electrode 50 which accelerates the secondary ions at a constant applied voltage, and a secondary electron multiplier 46 spaced by a constant distance L from the electrode 50 to detect the secondary ions.

The laser plasma radiation source is regarded as an ideal pulse radiation source because its laser pulse width is 10 nm sec or less. Hence, the secondary ions produced substantially at the same time as the laser pulse is produced begin to be made fly with the velocity corresponding to the ionic valence number and the mass number by the electrode 50 and after flying by the distance L, will be detected by the secondary electron multiplier 46. If, therefore, the time of detection at the secondary electron multiplier 46 which is a detector are measured based on the time of laser pulse generation set as an initial time, what and how many ions are emitted can be determined.

In the second embodiment, as stated above, the fact that the laser plasma radiation source is an ideal pulse radiation source is utilized for performing the time-of-flight measurement, and thus its detecting system can be extremely simplified. On the contrary, if the SR source were used as the radiation source, idealized pulse radiation could not be produced which brings about the pulse radiation by chopping the beam mechanically. Since the analysis based on the time-of-flight spectrometry deteriorates the resolving power at the time of flight, the time-of-flight spectrometry cannot be utilized. The ordinary SIMS, although capable of producing the ideal pulse by applying the magnetic field or the electric field to an electron beam of the probe, has the drawback that this brings about destructive analysis.

Thus, according to the second embodiment, the adsorbed substances on the sample surface can be analyzed two-dimensionally with a high resolving power, followed by a considerable simplification and downsizing of the apparatus. For the optical condensing system, the zone plate shown in FIG. 5 may of course be used.

For controlling measurement, a circuit arrangement according to FIG. 9 or FIG. 10 is applicable to the second embodiment also.

Figure 13:
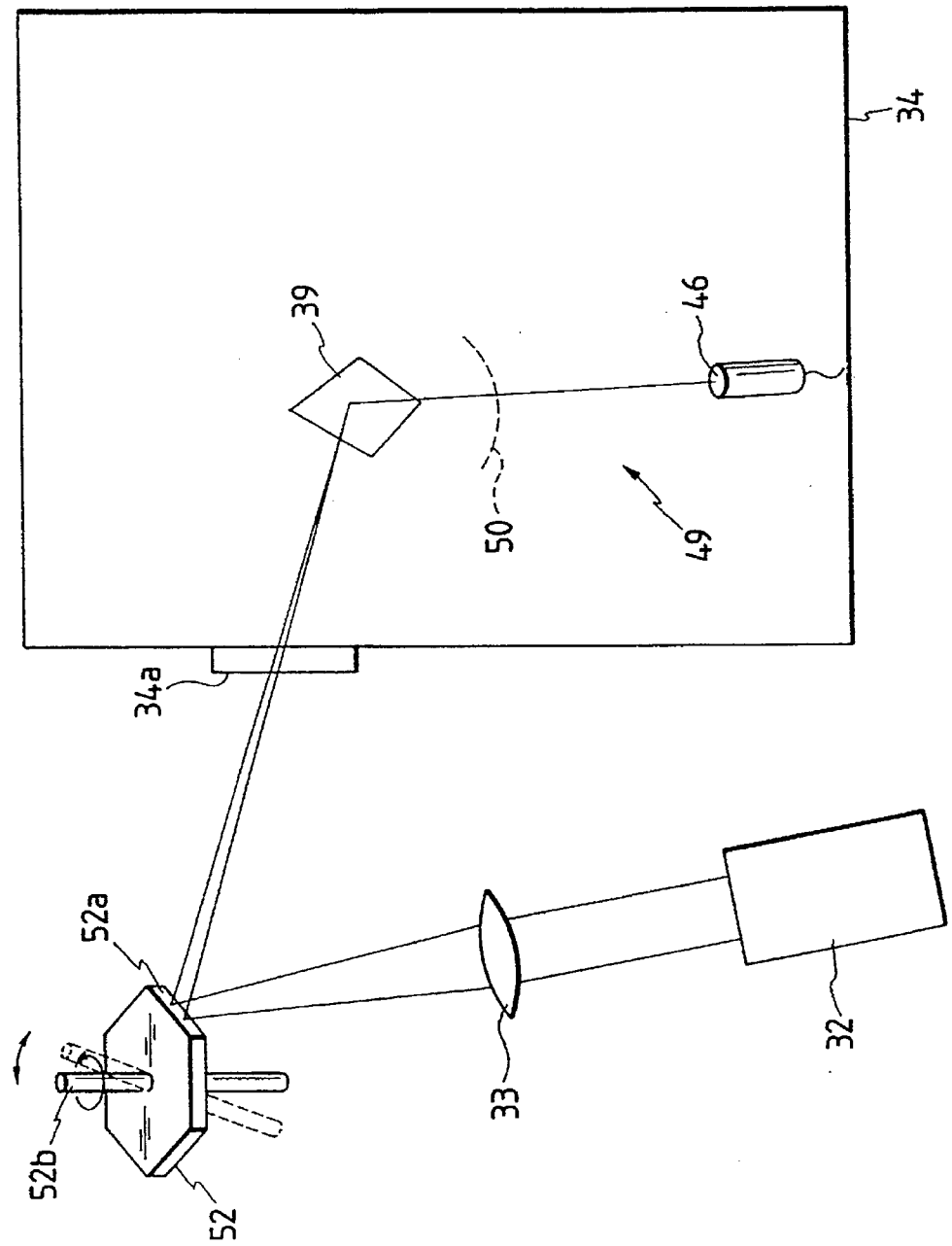
FIG. 13 is a view showing the arrangement of a third embodiment of the present invention.

In accordance with FIG. 13, a third embodiment of the present invention is explained. This embodiment uses the Nd:YAG laser 32 as the radiation source, and the laser beam emitted front the Nd:YAG laser 32 irradiates a polygonal rotating mirror 52 which is the optical deflecting system through the collector lens 33. The polygonal rotating mirror 52 has a plurality of mirror surfaces 52a for reflecting the laser radiation and a rotary shaft 52b. A rotation of the mirror 52 and a deflection of the rotary shaft 52b in a direction normal to that of the rotation have the result that the laser beam is concentrated on the surface of the sample 39 in the vacuum chamber 34 and can perform scanning two-dimensionally. On the orbit of the secondary ions produced from the surface of the sample 39 in the vacuum chamber 34 is disposed the time-of-flight spectrometer 49 having the secondary ion extracting electrode 50 and the secondary electron multiplier 46.

In the third embodiment of the foregoing arrangement, when the laser pulse is emitted from the Nd:YAG laser radiation source 32, the laser beam is transmitted through the collector lens 33, reflected by the polygonal rotating mirror 52, and converged on the sample 39 in the vacuum chamber 34. The laser beam, reflected by the mirror surface 52a of the polygonal rotating mirror 52, is such that its irradiation point scans the sample surface in response to the angle of rotation and the deflection of the mirror 52. The Nd:YAG laser radiation source 32, because its laser pulse width is less than 10 nm sec, is regarded as an ideal pulse radiation source, and hence the production of the secondary ions from the surface of the sample 39 will practically coincide with the emission of the laser pulse. The secondary ions begin to be made fly with the velocity according to the ionic valence number and the mass number by the electrode 50 of the time-of-flight spectrometer 49 and after flying by the distance L, are detected by the secondary electron multiplier 46. If, therefore, the time of detection at the secondary electron multiplier 46 which is a detector and signal intensity at that time, are measured based on the time of laser pulse generation set as an initial time, what and how many ions are emitted can be determined. Further, if the intensity of the laser beam with which the sample surface is irradiated is sufficiently decreased, the adsorbed substances on the surface can be dissociated and analyzed in the nondestructive way. In contrast to this, if the intensity of the laser beam is adjusted and the sample 39 is repeatedly irradiated with the laser beam at the same position for analysis, the information of the sample 39 in the direction of depth can be brought about.

In the third embodiment, as mentioned above, the system arrangement for analysis is extremely simplified compared with the SIMS and ESD and the nondestructive analysis, such as that in the PSD, is also possible. Hence, the adsorbed substances on the sample surface can be analyzed two-dimensionally with a high resolving power in the destructive or nondestructive way. The laser beam, which is an ideal pulse radiation, enables the ion analysis based on the time-of-flight spectrometry with a considerable degree of accuracy.

Figure 14:
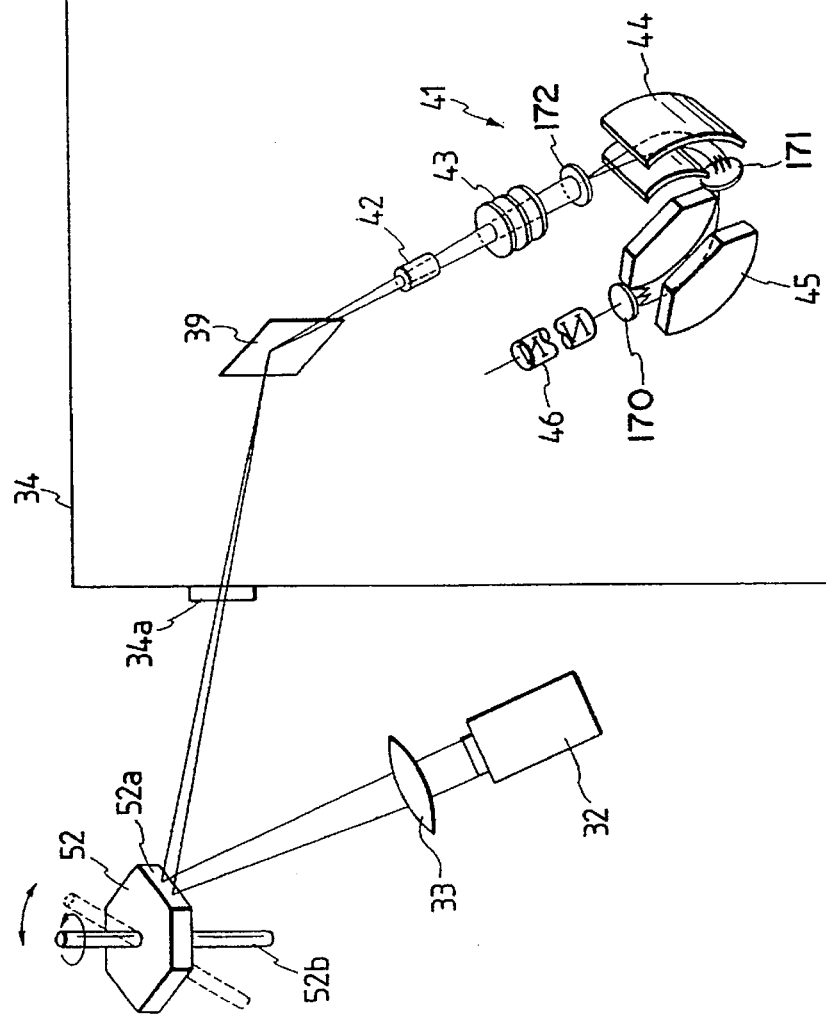
FIG. 14 is a view showing the arrangement of a fourth embodiment of the present invention.

FIG. 14 is a schematic view showing the arrangement of a fourth embodiment of the present invention. This embodiment is similar in arrangement to the third embodiment using the laser radiation source, but is equipped with the mass spectrometer 41, instead of the time-of-flight spectrometer 49, in the vacuum chamber 34, thereby permitting the mass analysis. Also shown in FIG. 14 are a collector slit 170, a β slit 171, and a slit 172.

For controlling measurement, a circuit arrangement according to FIG. 9 or FIG. 10 is applicable to the fourth embodiment also.

Also, in the embodiments which have been described, fluorescent X rays, photoelectrons, and Auger electrons are produced at the same time and, by monitoring such information, the surface analyzing apparatus providing a larger amount of information will be derived.

Next, a fifth embodiment of the present invention is explained. In this embodiment, the sample is irradiated with corpuscular radiation in a sample chamber to emit the secondary electrons, which are detected through an electron spectrometer by a detector, and the spectrum of the secondary electrons are measured. In this case, a gas with a known secondary electron resonance line is introduced into the sample chamber, which is then sealed up, and the measured value of energy of the secondary electrons emitted from the sample is calibrated based on that of energy of the secondary electron resonance line.

In such spectrometry, the electron spectrometer is such that although the measured value of energy to be analyzed fluctuates according to the change of an internal space potential, the amount of fluctuation of energy is the same in regard to any secondary electron. Hence, the gas having the known secondary electron resonance line is sealed up within the sample chamber to make the measurement, and the measured value of energy of the secondary electrons emitted from the sample is calibrated based on the difference between an ideal value of energy of the known secondary electron resonance line (Auger, auto-ionization, or photoelectrons) and a value of energy of the actual secondary electron resonance line actually measured. Thus, it is possible to accurately determine the absolute value. Here, for the gas having the known secondary electron resonance line to be introduced into the sample chamber, rare gas (He, Ne, Ar, Kr, Xe, or Rn) and the like are available.

FIG. 15 shows an example of the arrangement of an electron spectrometer following the secondary electron spectrometry which is the fifth embodiment of the present invention. In this embodiment, laser beam from a YAG laser radiation source 61 passes through a collector lens 62 and a window 64 disposed in a vacuum chamber 63 and is converged on a target 65 rotatably disposed within the vacuum chamber 63. In this way, a part of the target 65 is converted into plasma to produce soft X rays. The soft X rays produced from the target 65 is monochronized by a concave diffraction grating 67 provided in a vacuum chamber 66 communicating to the vacuum chamber 63, and is then introduced into a vacuum sample chamber 68 communicating with the vacuum chamber 66. The vacuum sample chamber 68 houses a slit 69, an X-ray optical system (Wolter mirror optical system) 70, a sample holder 72 supporting a sample 71, an electron spectrometer 73, and a MCP 74. The whole of the vacuum sample chamber 68 is movably mounted to the vacuum chamber 66 so that the slit 69 can move along the Rowland circle of the grating 67. The electron spectrometer 73, as shown in FIG. 16, is of a coaxial cylinder static type having an entrance slit 75 and an exit slit 76, and two cylindrical electrodes 77 and 78 provided as secondary electrons deflecting means between these slits, being held by a support 79. The sample holder 72 is provided to be movable in a two-dimensional direction, with respect to the support 79, in a plane normal to the direction of incidence of the X rays. Also shown in FIG. 15 is the Rowland radius 180.

In this way, the vacuum sample chamber 68 is moved in regard to the vacuum chamber 66 to select the X rays of desired wavelengths traversing the slit 69, and the sample 71 is irradiated with the resultant X rays through the X-ray optical system 70. The secondary electrons thus emitted are detected by the MCP 74 while the electron spectrometer 73 performing sweep operation with respect to voltage applied to the two cylindrical electrodes 77 and 78 thereof. The sweep of the voltage applied to the two cylindrical electrodes 77 and 78 brings the result that, of charged particles incident from the entrance slit 75, a particle with particular kinetic energy responding to the applied voltage is deflected to follow a circular orbit across the electrodes, emerges from the exit slit 76, and enters the MCP 74. In the fifth embodiment, a cover 80 is provided between the vacuum chamber 66 and the vacuum sample chamber 68 so that they communicate with each other through the slit 69. Further, a gas injector 81 is connected to the vacuum sample chamber 68. As such, prior to the analysis of the secondary electrons of the sample 71, the vacuum sample chamber 68 is sealed up upon Kr gas being introduced thereinto. Here, a vacuum state of the vacuum chambers 63 and 66 and the vacuum sample chamber 68 is assumed to be $10^{-4} \sim 10^{-5}$ Torr.

Thus, the spectrum of the secondary electrons is measured in the state where Kr gas is introduced into the vacuum sample chamber 68. The difference between the energy value of the known secondary electron resonance line of the Kr gas and the actual measured value is detected and subtracted from the measured value of energy of the secondary electrons emitted from the sample 71. Whereby, the measured value of energy of the secondary electrons is calibrated and the absolute value is determined.

Figure 17:
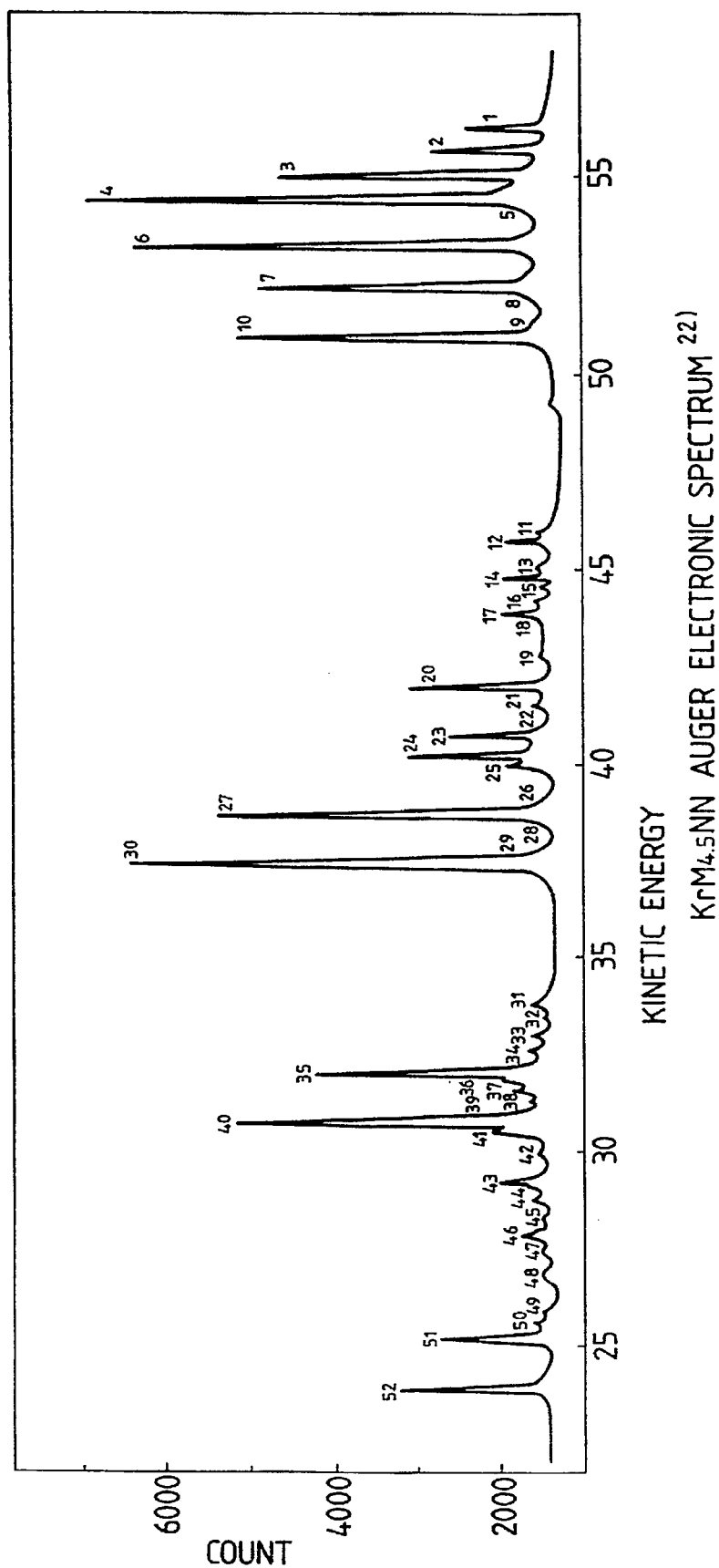
FIG. 17 is a diagram showing kinetic energy in an Auger electron spectrum.

FIG. 17 shows an energy spectrum representing MNN Auger electron resonance lines of Kr gas by X-ray impact. The energy resonance lines are known and there is little signal due to ionization except the resonance lines, so that background noise caused in analyzing the secondary electrons of the sample 71 can be considerably decreased. If, therefore, the difference is found between the energy value of the known secondary electron resonance line of Kr gas and the actual measured value, an undesired fluctuation of energy in the electromagnetic field caused within the electron spectrometer 73 can be known. By subtracting the value of such fluctuation from the measured value of energy of the secondary electrons of the sample 71, the absolute value of energy of the secondary electrons of the sample 71 can be accurately determined.

Figure 18:
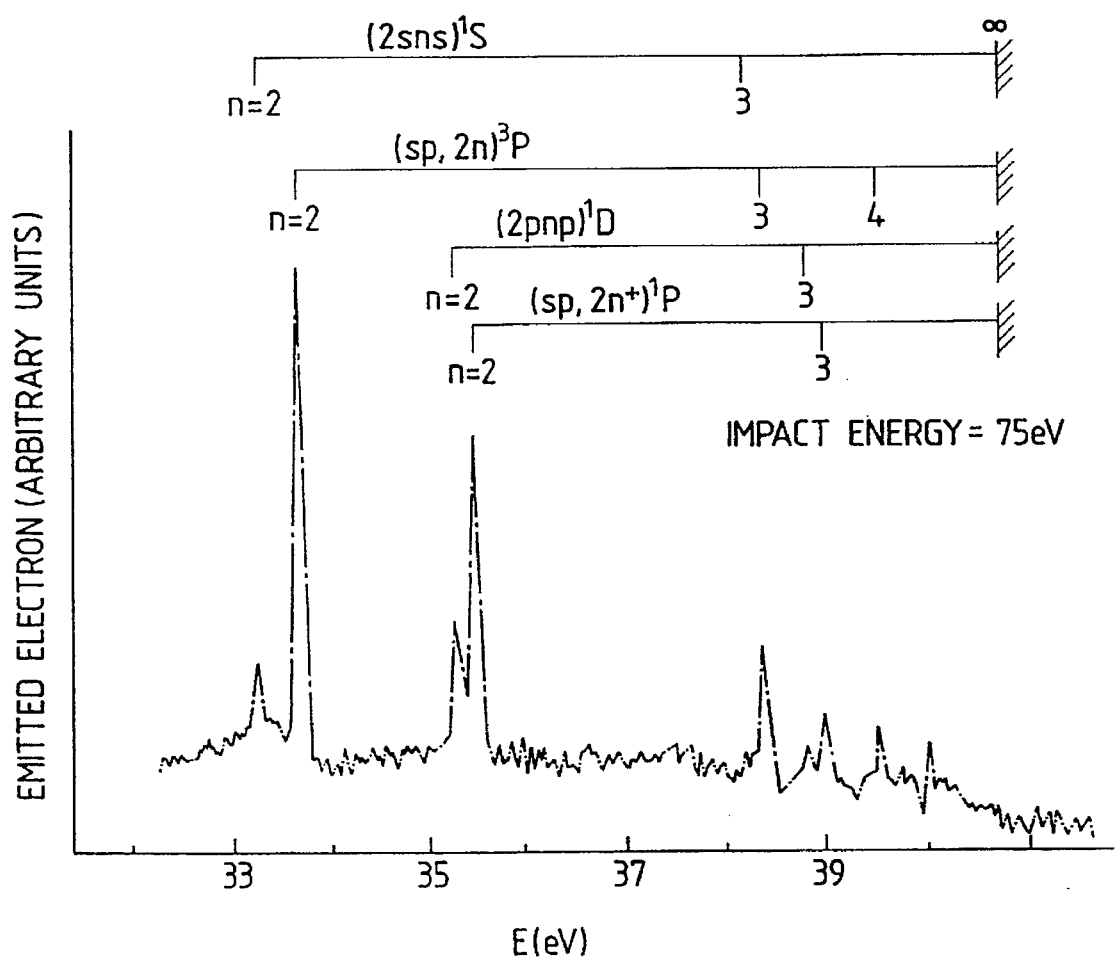
FIG. 18 is a diagram showing the energy spectrum of lines automatic ionizing resonance line of an He gas in electron impact.

The kind of gas introduced into the vacuum sample chamber 68 in the measurement can properly be selected in accordance with the corpuscular radiation impacting the sample 71. For example, where the electron is used, the auto-ionization resonance lines of He gas can be applied. The auto-ionization resonance lines of He gas in the spectrum, as depicted in FIG. 18, appear only at 40 eV or less. If they are used for calibration, the absolute value of energy of the secondary electrons of the sample 71 can be determined with accuracy.

Figure 19:
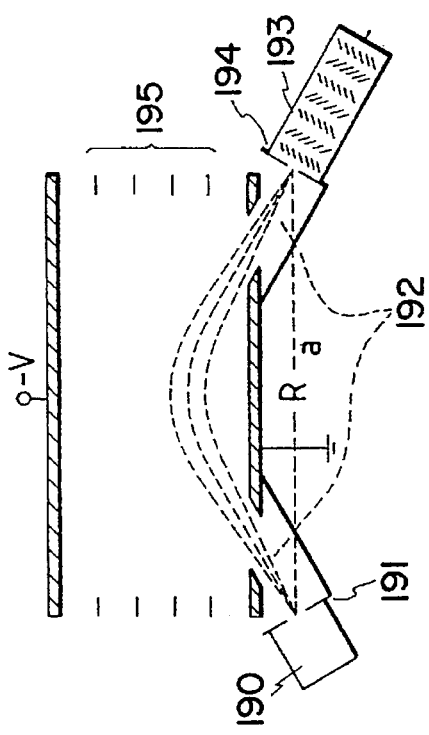
FIGS. 19 to 22 are views showing electron spectrometers of other types.
Figure 20:
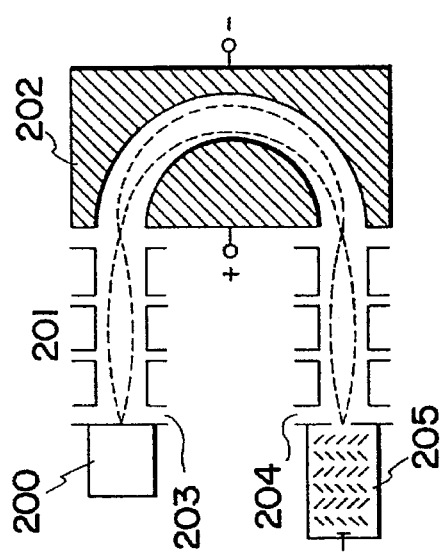

The electron spectrometer 73 may be of the types shown in FIGS. 19 to 22, not to speak of the coaxial cylinder static type shown in FIG. 16. FIG. 19 illustrates a plane-parallel static electron spectrometer. This electron spectrometer is designed so that a voltage applied across two electrodes causes the deflection of a particle having particular kinetic energy responding to the applied voltage, of charged particles entering by an entrance slit, and the particle is detected through an exit slit by a detector (electron multiplier). The sweep of the applied voltage makes it possible to analyze the energy spectrum of the charged particles. Also shown in FIG. 19 are: an ionization chamber 190, an entrance slit 191, the field-free space 192, an electron multiplier 193, an exit slit 194, and a boundary electric field compensating electrode 195. FIG. 20 shows a hemispherical static electron spectrometer. FIG. 20 also shows an ionization chamber 200, a lens system 201, a concentric hemispherical spectroscope 202, slits 203, 204, and an electron multiplier 205. This electron spectrometer, although similar in principle to the coaxial cylinder static electron spectrometer in FIG. 16, has the advantage that its spherical electrode permits the energy analysis of charged particles at various angles of incidence.

Figure 21:
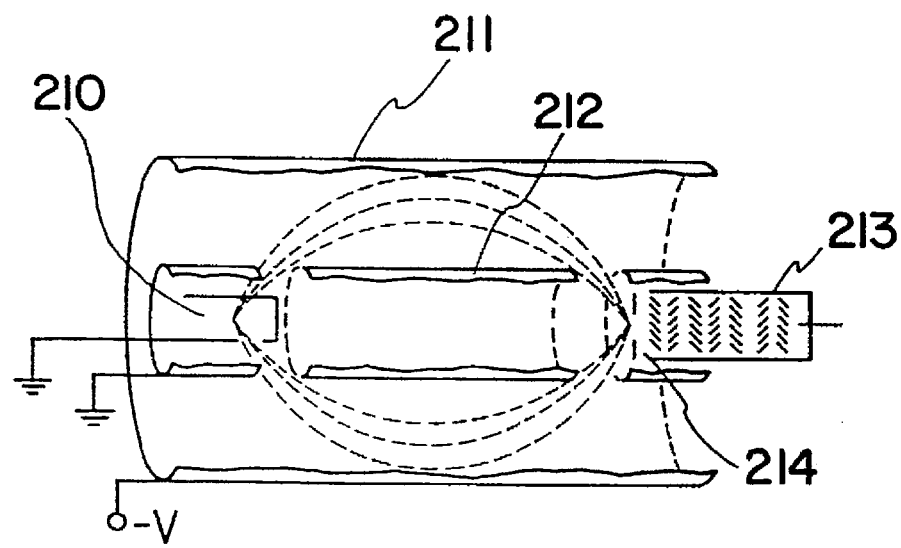
Figure 22:
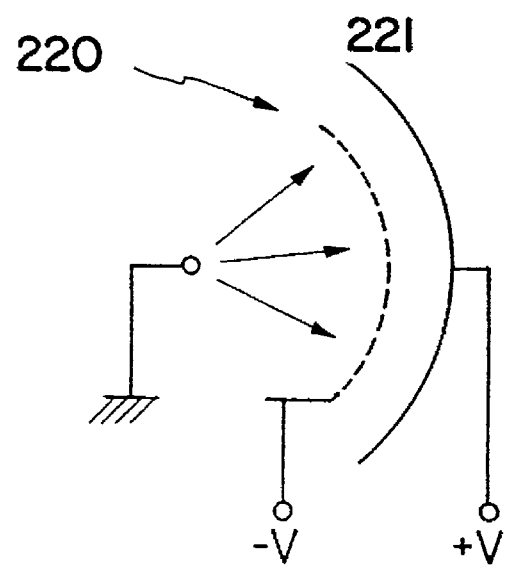

FIG. 21 depicts a cylindrical mirror static electron spectrometer. This electron spectrometer, although similar in principle to the plane-parallel static electron spectrometer in FIG. 19, has the advantage that its cylindrical electrode permits the energy analysis of charged particles at various angles of incidence as in FIG. 20. FIG. 21 also shows an ionization chamber having point source 210, an outer cylinder 211, an inner cylinder 212, an electron multiplier 213, and a slit 214. FIG. 22 shows a field blocking static electron spectrometer. This electron spectrometer is fundamentally constructed so that the potential of the sample emitting the charged particles is grounded, a polarity potential attracting the charged particles to an opposed electrode is provided, a grid between the sample and the opposed electrode is provided with a potential for repelling the charged particles, and the charged particle exceeding the particular kinetic energy passing through the grid and reaching the opposed electrode is detected as a current flowing between the opposed electrode and the grounding. By sweeping the potential of the grid and taking the difference of its current value, the energy analysis of the secondary electrons can be made. FIG. 22 also shows a grid 220 and an anode 221.

Although, in FIG. 15, the MCP 74 is used as the detector, the electron multiplier may well be employed. In FIGS. 19 to 21, the use of the MCP is also possible. Further, the electron spectrometer which deflects the charged particles in the magnetic field may be used where the kinetic energy of the charged particles to be analyzed is particularly high.

Next, reference is made to a sixth embodiment of the present invention. In this embodiment, the sample is irradiated with the corpuscular radiation in a pulse mode to emit the secondary electrons, which are made incident on the detector through the electron spectrometer. Subsequently, based on the peak value of the output signal of the detector, the secondary electrons emitted from the sample are analyzed. In such formation, when the secondary electrons discharged from the sample by the pulse-mode irradiation with the corpuscular radiation are detected by the detector and its peak value is found, the value is proportional to the number of the secondary electrons produced, having the same ability as a pulse counting method. Hence, the secondary electrons discharged from the sample can be analyzed based on the peak value.

Figure 23:
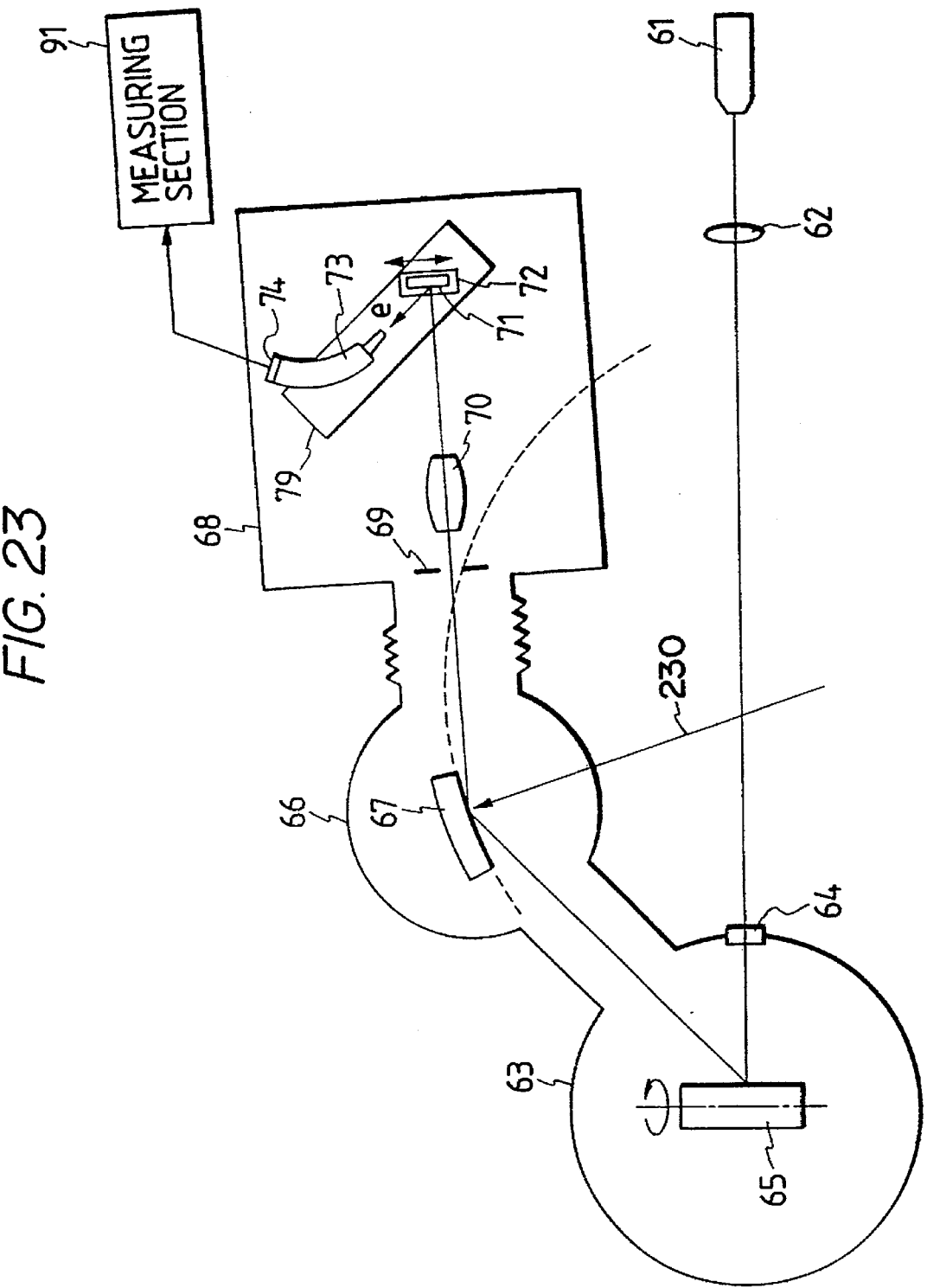
FIG. 23 is a view showing the arrangement of a sixth embodiment according to the present invention for analyzing the secondary electron.
Figure 24:
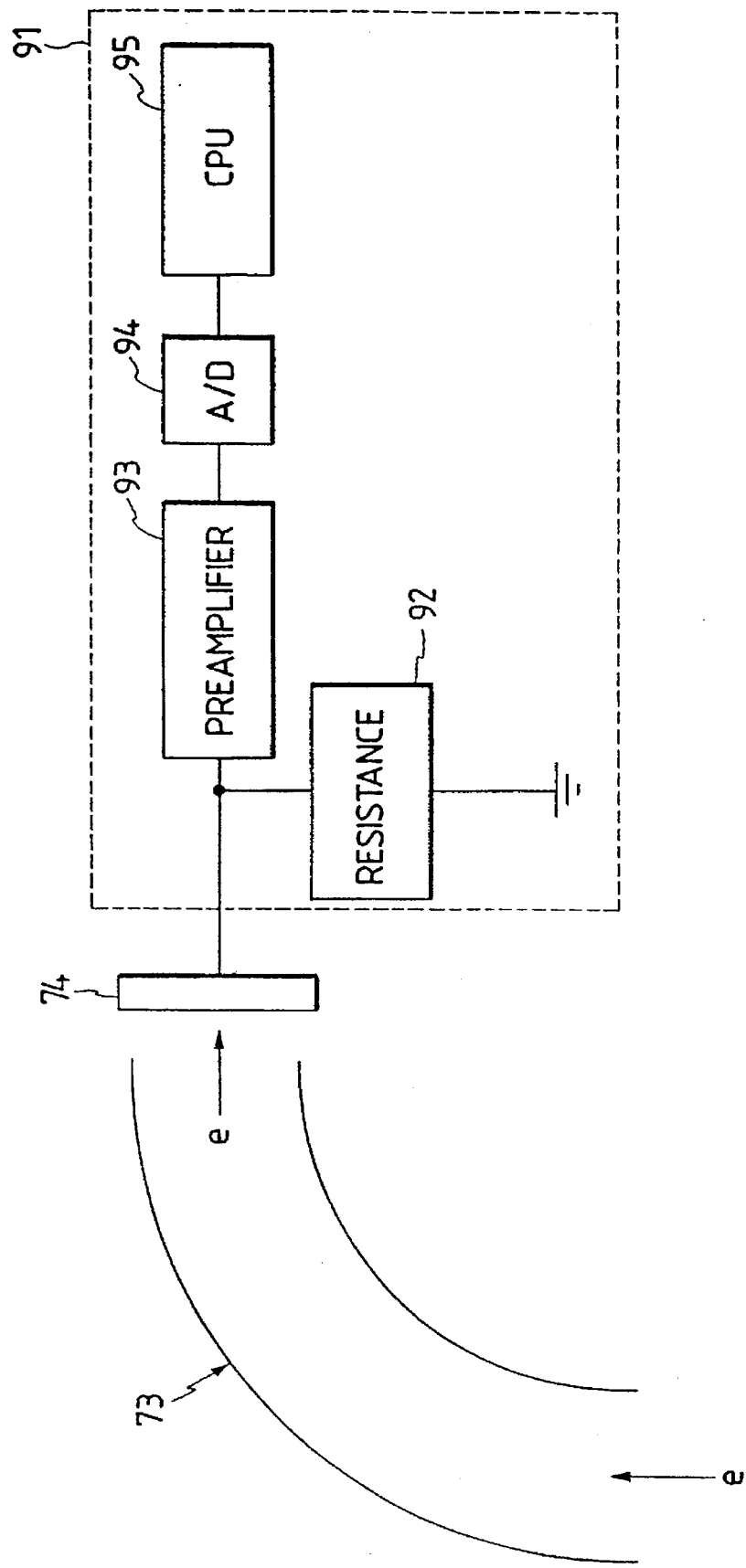
FIG. 24 is a view showing a measuring section in the sixth embodiment.

In FIG. 23 showing the sixth embodiment, the output of the MCP 74 is supplied to a measuring section 91 to analyze the secondary electrons emitted from the sample 71. FIG. 23 also shows the Rowland radius 230. The measuring section 91, as shown in FIG. 24, incorporates a resistance 92, a preamplifier 93, an A/D converter 94, and a CPU 95. By the floating capacity of the MCP 74 and an integrating circuit composed of the resistance 92, the electric charge generated at the MCP 74 is integrated and converted into the peak value of the voltage. Subsequently, the peak value is amplified by the preamplifier 93 and converted into a digital signal by the A/D converter 94 so that the secondary electrons are analyzed at the CPU 95. In this way, the laser radiation is emitted from the YAG laser radiation source 61 in a pulse mode, and the soft X rays produced at the target 65, after passing through the concave diffraction grating 67, the slit 69, and the X-ray optical system 70, irradiate the sample 71. The secondary electrons thus discharged are detected through the electron spectrometer 73 by the MCP 74 and are analyzed at the measuring section 91.

Hence, according to the sixth embodiment, the analysis of the sample 71 can be variously made with high accuracy. Since a high-speed pulse measurement, such as that in the pulse counting method, is not made, the circuit configuration of the measuring section 91 can be simplified and made low in cost. Further, if a circuit arrangement similar to that shown in FIG. 10 is adopted and Q switch signal by which the YAG laser radiation source 61 is driven to emit the laser pulse is synchronized with the measuring timing in the measuring section 91 so that the sample 71 is irradiated with the X-ray pulse several times, the peak value for each time can also be measured and integrated. Thus, it is possible to make the analysis with high accuracy.

In addition to the coaxial cylinder static type shown in FIG. 16, the types shown in FIGS. 19 to 21 can be used as the electron spectrometer 73.

What is claimed is:

1. A surface analyzing apparatus comprising:
   a laser plasma radiation source comprising:
      a laser utilizing a Q switch signal, and
      external trigger signal generating means, controlled by a CPU, for generating control signal sets in sequence to thereby cause said laser to radiate a laser beam in pulse mode;
   an optical condensing system for converging radiation emanating from said laser plasma radiation source on a surface of a sample, said radiation being one of ultraviolet light, vacuum ultraviolet light, and X rays; and
   a mass spectrometer for detecting secondary ions emitted from said sample, said mass spectrometer including:
      secondary ions deflecting means for deflecting said secondary ions emitted from said sample, said secondary ions deflecting means including:
         deflection amount control means for controlling an amount of deflection of said secondary ions in accordance with a number of said control signal sets generated.

2. A surface analyzing apparatus according to claim 1, wherein:
   each of said control signal sets includes a plurality of control signals, each of said plurality of control signals triggering said laser to emit a pulse of said laser beam.

3. A surface analyzing apparatus according to claim 1, wherein:
   each of said control signal sets includes a signal for triggering said laser to emit a plurality of pulses of said laser beam.

4. A surface analyzing apparatus comprising:
   a laser plasma radiation source comprising:
      a laser utilizing a Q switch signal, and
      an external pulse generator, controlled by a CPU, to generate signal sets which cause said laser to emit a pulsed laser beam;
   an optical condensing system for converging radiation emanating from said laser plasma radiation source on a surface of a sample, said radiation being one of ultraviolet light, vacuum ultraviolet light, and X rays; and
   a mass spectrometer for detecting secondary ions emitted from said sample, said mass spectrometer including:
      secondary ions deflecting means for deflecting said secondary ions emitted from said sample, and
      deflection amount control means for controlling an amount of deflection of said secondary ions so as to be a first value after a first signal set is generated from said external pulse generator, and then to be a second value different from said first value after a second signal set is generated from said external pulse generator, thereby making mass spectrometry of said secondary ions possible.

5. A surface analyzing apparatus according to claim 4, wherein:
   said first signal set and said second signal set from said external pulse generator respectively cause a first sequence and a second sequence of emission of said pulsed laser beam, said first sequence and second sequence of emission of said pulsed laser beam respectively causing a first sequence and a second sequence of emission of said radiation which is one of said ultraviolet light, said vacuum ultraviolet light, and said X rays, said first sequence and said second sequence of emission of said radiation respectively causing a first sequence and a second sequence of emission of said secondary ions from said sample, and then detection is made respectively for said first sequence and said second sequence of emission of said secondary ions with said amount of deflection of said secondary ions being controlled to be said first value and said second value respectively.

6. A surface analyzing apparatus according to claim 4, further comprising:
   a stage for mounting said sample; and
   stage drive means for moving said stage in X and Y directions for allowing mass spectrometry of said sample in said X and Y directions.

7. A surface analyzing apparatus according to claim 4, wherein:
   each of said first signal set and said second signal set includes a plurality of signals; and
   each of said first sequence and said second sequence of emission of said secondary ions to be detected at one time includes a plurality of occurrences of emission of said secondary ions, with a number of said occurrences corresponding to a number of said signals included in each of said first signal set and said second signal set.

8. A surface analyzing apparatus according to claim 4, wherein:
   said deflection amount control means controls said deflection amount of said secondary ions to be said first value and said second value by controlling both of a voltage and a magnetic field applied.

9. A surface analyzing apparatus according to claim 4, wherein:
   said deflection amount control means controls said deflection amount of said secondary ions to be said first value and said second value by controlling at least one of a voltage and a magnetic field applied alternatively.

10. A surface analyzing apparatus according to claim 4, wherein said laser plasma radiation source further comprises:
    a target which is irradiated with said pulsed laser beam from said laser to generate plasma, said radiation being generated from said plasma.

11. A surface analyzing apparatus according to claim 10, further comprising:
    a vacuum chamber housing said target, said optical condensing system, said sample, and said mass spectrometer.

12. A surface analyzing apparatus comprising:
    a vacuum chamber;
    a laser plasma radiation source, said laser plasma radiation source including:
       a laser utilizing a Q switch signal for generating a pulsed laser beam,
       an external pulse generator, controlled by a CPU, to generate signal sets which cause said laser to generate said pulsed laser beam, and
       a target which is irradiated with said pulsed laser beam from said laser to generate plasma, said irradiation being one of ultraviolet light, vacuum ultraviolet light, and X rays being generated from said plasma;

an optical condensing system for converging said radiation emanating from said laser plasma radiation source on a surface of a sample;

a stage for mounting said sample;

stage drive means for moving said stage in X and Y directions; and a mass spectrometer for detecting secondary ions emitted from said sample, said mass spectrometer including:

secondary ions deflecting means for deflecting said secondary ions emitted from said sample, and deflection amount control means for controlling an amount of deflection of said secondary ions, thereby making mass spectrometry of said secondary ions possible;

wherein said radiation is converged on one spot on said surface of said sample;

wherein said surface of said sample can be scanned two-dimensionally with said spot on which said radiation is converged being displaced in accordance with movement of said stage in said X and Y directions caused by said stage drive means; and wherein said vacuum chamber houses said target, said optical condensing system, said stage, said stage drive means, and said mass spectrometer.

13. A surface analyzing apparatus comprising:

a laser plasma radiation source, said laser plasma radiation source including:

a laser utilizing a Q switch signal, and external trigger signal generating means, controlled by a CPU, for generating control signal sets in sequence to thereby cause said laser to emit a laser beam in pulse mode;

an optical condensing system for converging radiation emanating from said laser plasma radiation source on a surface of a sample, said radiation being one of ultraviolet light, vacuum ultraviolet light, and X rays; and an electron spectrometer for detecting secondary electrons emitted from said sample, said electron spectrometer including secondary electrons deflecting means for deflecting said secondary electrons emitted from said sample, said secondary electrons deflecting means including deflection amount control means for controlling an amount of deflection of said secondary electrons in accordance with a number of said control signal sets generated.

14. A surface analyzing apparatus comprising:

a laser utilizing a Q switch signal;

external trigger signal generating means, controlled by a CPU, for generating control signal sets in sequence to thereby cause said laser to radiate a laser beam in pulse mode;

an optical condensing system for converging said laser beam from said laser on a surface of a sample; and a mass spectrometer for detecting secondary ions emitted from said sample, said mass spectrometer including secondary ions deflecting means for deflecting said secondary ions emitted from said sample, said secondary ions deflecting means including deflection amount control means for controlling an amount of deflection of said secondary ions in accordance with a number of said control signal sets generated.

15. A method of analyzing a surface, including the steps of:

generating a pulsed laser beam based on Q switched signals externally actuated under control of a CPU;

generating pulsed corpuscular radiation by irradiating a target with said pulsed laser beam;

irradiating a sample with said pulsed corpuscular radiation to cause said sample to emit secondary ions; and causing said secondary ions to be incident on a detector through a mass spectrometer comprising secondary ions deflecting means which deflects said secondary ions; and controlling an amount of deflection of said secondary ions through said secondary ions deflecting means to be a first value synchronized with a generation of a first signal of said control signals so that said secondary ions having energy proportional to said first value of said amount of deflection are selected for analysis.

16. A method of analyzing a surface according to claim 15, further including the steps of:

displacing a spot on a surface of said sample to be irradiated with said pulsed corpuscular radiation in X and Y directions; and repeating said steps of generating said pulsed laser beam, generating said pulsed corpuscular radiation, irradiating said sample, and causing said secondary ions to be incident on said detector so as to achieve a two-dimensional analysis of said sample;

said step of irradiating said sample includes a step of converging said pulsed corpuscular radiation on said spot on said surface of said sample for irradiation.

17. A method of analyzing a surface, including:

generating a pulsed laser beam in accordance with Q switched signals externally actuated under control of a CPU;

generating pulsed corpuscular radiation by irradiating a target with said pulsed laser beam;

irradiating a sample with said pulsed corpuscular radiation to make said sample emit secondary electrons; and causing said secondary electrons to be incident on a detector through an electron spectrometer comprising secondary electrons deflecting means which deflects said secondary electrons;

wherein an amount of deflection of said secondary electron through said secondary electrons deflecting means is controlled to be a first value synchronized with generation of a first signal of said externally Q switched signals so that secondary electrons having energy proportional to said first value of an amount of deflection are selected for analysis.

18. A method of analyzing a surface according to claim 17, further including steps of:

displacing a spot on a surface of said sample to be irradiated with said pulsed corpuscular radiation in X and Y directions; and repeating said steps of generating a pulsed laser beam, generating said pulsed corpuscular radiation, irradiating said sample, and causing said secondary electrons to be incident on said detector so as to achieve a two-dimensional analysis of said sample;

said step of irradiating said sample including a step of converging said pulsed corpuscular radiation on said spot on said surface of said sample for irradiation.

19. A method of analyzing a surface according to claim 17, further including the steps of:

setting said sample inside a sample chamber;

sealing said sample chamber upon introducing a gas having a known secondary electron resonance line thereinto; and calibrating a measured value of energy of said secondary electrons emitted from said sample based on a measured value of energy of said secondary electron resonance line of said gas.

* * * * *